United States Patent
Shani et al.

(12) 
(10) Patent No.: US 6,331,416 B1
(45) Date of Patent: Dec. 18, 2001

(54) PROCESS OF EXPRESSING AND ISOLATING RECOMBINANT PROTEINS AND RECOMBINANT PROTEIN PRODUCTS FROM PLANTS, PLANT DERIVED TISSUES OR CULTURED PLANT CELLS

(75) Inventors: Ziv Shani, Rehovot; Oded Shoseyov, Karme Yosef, both of (IL)

(73) Assignees: CBD Technologies Ltd., Rehovot; Yissum Research and Development Company of the Hebrew University of Jerusalem, Jerusalem, both of (IL)

( * ) Notice: Subject to any disclaimer, the term of this patent is extended or adjusted under 35 U.S.C. 154(b) by 0 days.

(21) Appl. No.: 09/329,234

(22) Filed: Jun. 10, 1999

(51) Int. Cl.$^7$ .......................... C07K 19/00; C12N 15/09; C12N 15/36
(52) U.S. Cl. .................... 435/69.7; 435/69.1; 435/172.3; 435/320.1; 435/252.3; 530/387.3; 536/23.4; 536/23.1
(58) Field of Search ................................ 435/69.1, 320.1, 435/252.3; 536/23.7, 23.1; 800/295

(56) References Cited

U.S. PATENT DOCUMENTS 5,719,044 * 2/1998 Shoseyov et al. .................. 435/69.7

OTHER PUBLICATIONS

E. Ong et al., Enzyme Microb. Technol., vol. 13, Jan. 1991, pp. 59–65.*
J. Greenwood et al., Federation of European Biochemical Societies, vol. 244, No. 1,Feb. 1989,pp. 127–131.*
J. Greenwood et al., Protein Engineering, vol. 5, No. 4, 1992, pp. 361–365.*

* cited by examiner

*Primary Examiner*—Bruce R. Campbell
*Assistant Examiner*—Joseph T. Woitach

(57) ABSTRACT

A process of expressing a recombinant protein in a plant and of isolating the recombinant protein from the plant, the process is effected by (a) providing a plant, a plant derived tissue or cultured plant cells expressing a fusion protein including the recombinant protein and a cellulose binding peptide being fused thereto, the fusion protein being compartmentalized within cells of the plant, plant derived tissue or cultured plant cells, so as to be sequestered from cell walls of the cells of the plant, plant derived tissue or cultured plant cells; (b) homogenizing the plant, plant derived tissue or cultured plant cells, so as to bring into contact the fusion protein with a cellulosic matter of the plant, plant derived tissue or cultured plant cells, to thereby effect affinity binding of the fusion protein via the cellulose binding peptide to the cellulosic matter, thereby obtaining a fusion protein cellulosic matter complex; and (c) isolating the fusion protein cellulosic matter complex.

11 Claims, 1 Drawing Sheet

PROCESS OF EXPRESSING AND ISOLATING RECOMBINANT PROTEINS AND RECOMBINANT PROTEIN PRODUCTS FROM PLANTS, PLANT DERIVED TISSUES OR CULTURED PLANT CELLS

FIELD AND BACKGROUND OF THE INVENTION

The present invention relates to a process of expressing and isolating recombinant proteins and recombinant protein products from plants, plant derived tissue or cultured plant cells, which process exploits (i) the high affinity between cellulose binding peptides and cellulose; (ii) the inherent abundance of cellulose in planta; and/or (iii) the simplicity associated with cellulose isolation from plants, plant derived tissue and cultured plant cells.

More particularly, the present invention relates to a process expressing and isolating recombinant proteins and recombinant protein products from plants, plant derived tissue or cultured plant cells, which process employs the expression of a fusion protein including a recombinant protein and a cellulose binding peptide fused thereto, plant homogenization, isolation of a fusion protein cellulosic matter complex and optional subsequent isolation of the fusion protein and/or the recombinant protein from the complex. The present invention further relates to nucleic acid molecules and to genetically modified or viral infected plants or plant cells which are useful while implementing the process, and further to a novel composition of matter which results from the process.

Citation or identification of any reference in this section or in any other section of this application shall not be construed as an admission that such reference is available as prior art to the present invention.

With the advent of recombinant technology, techniques for the genetic transformation of various host organisms, such as bacteria, yeasts, fungi, plants and animals, for the purposes of producing specific proteins through the expression of heterologous or foreign genes have been extensively developed.

Using these recombinant techniques and hosts, numerous commercially important recombinant proteins (examples of which are included hereinbelow) have been expressed and purified. Expression and isolation of a protein of interest on a commercial scale, neccesitate the selection of a suitable expression host. This selection largely depends on the economics of production and purification, as well as the ability of the host to accomplish the post-translational modifications needed for full biological activity of the recombinant protein.

Much of the early work in biotechnology was directed toward the expression of recombinant or "heterologous" proteins in prokaryotes like *Escherichia coli* and *Bacillus subtilis* because of the relative ease of genetic manipulation, growth in batch culture and large-scale fermentation of prokaryotes.

Although *E. coli* can in certain cases perform some post translational modifications and events, such as, protein folding and disulfide bond formation, it cannot secrete proteins extracellularly nor can it glycosylate, gamma carboxylate, beta hydroxylate, acetylate or process pre- and pro- peptides. *B. subtilis* suffers from the same limitations as *E. coli* except that it is capable of extracellular secretion.

Furthermore, *E. coli* and other bacteria are pathogens and therefore, depending on the application, contaminants such as pyrogens and endotoxins expressed along with the recombinant protein must be removed In addition, extensive post-purification chemical and enzymatic treatments (e.g., to refold the protein into an active form) are sometimes required in order to obtain a biologically active protein.

Because proteins are not secreted from prokaryotes like *E. coli*, bacterial cells must be disrupted for product recovery. The subsequent release of bacterial contaminants and other proteins make product purification more difficult and expensive. Because purification accounts for up to 90% of the total cost of producing recombinant proteins in bacteria, proteins like Insulin can cost several thousand dollars per gram when recombinantly produced in, and subsequently isolated from, *E. coli*.

Because of the many limitations associated with prokaryotic hosts, the biotechnology industry has looked for eukaryotic host cultures such as, yeast, fungi, insect cells, and mammalian cell tissue culture, to properly and efficiently express recombinant proteins.

For most of the proteins requiring extensive post-translational modifications for therapeutic and/or functional activity, mammalian cell culture is the most common alternative to *E. coli*. Although mammalian cells are capable of correctly folding and glycosylating bioactive proteins, the quality and extent of glycosylation can vary with different culture conditions among the same host cells. Furthermore, mammalian culture has extremely high fermentation costs (60–80% of total production expense), requires expensive media, and poses safety concerns from potential contamination by viruses and other pathogens. Yields are generally low and in the range of 0.5–1.5% of cellular protein, or micrograms per liter (up to 300–400 milligrams per liter).

Yeast, other fungi, and insect cells are currently being used as alternatives to mammalian cell culture. Yeast, however, produces incorrectly glycosylated proteins that have excessive mannose residues and are generally limited in eukaryotic processing. Further, although the baculovirus insect cell system can produce high levels of glycosylated proteins, these are typically not secreted, making purification complex and expensive. Fungi represent the best current system for high-volume, low-cost production of recombinant proteins, but they are not capable of expressing many target proteins.

In addition, eukaryotic cultures, require the maintenance of suitable conditions for efficient commercially viable expression of proteins. As such, the ambient temperature, pH value and aeration level of such cultures need to be carefully controlled, while nutrients must be added to the culture medium in carefully regulated doses and waste products removed. In addition, rigorous aseptic practices must be observed in order to avoid contamination by extraneous microbes. Such cultures are thus normally grown in sophisticated fermentors or bioreactors which are housed in expensively maintained factories. Such overheads are reflected in the high price of the recombinant protein end-products.

To a lesser extent, animals have also been utilized for the production of recombinant proteins. Although large amounts of protein can be produced and relatively easily recovered from such animals (e.g., proteins specifically produced in mammary glands and secreted with the milk), production in such host is limited to the expression of proteins which do not interfere with the host physiology. In addition, transgenic animals are subject to lengthy lead times to develop herds with stable genetics, high operating costs, contamination by animal viruses and a relatively slow rate of biomass generation substantially prolonging the time period following which recovery of commercial amounts of the protein can be effected.

The biochemical, technical and economic limitations on existing prokaryotic and eukaryotic expression systems has created substantial interest in developing new expression systems for the production of recombinant proteins.

Plants represent the most likely alternative to existing expression systems. With the availability and on going development of plant transformation techniques, most commercially important plant species can now be genetically modified to express a variety of recombinant proteins.

Such transformation techniques include, for example, the Agrobacterium vector system, which involves infection of the plant tissue with a bacterium (Agrobacterium) into which the foreign gene has been inserted. A number of methods for transforming plant cells with Agrobacteriumn are well known (Klee et al., Annu. Rev. Plant Physiol. (1987) 38:467–486; Schell and Vasil Academic Publishers, San Diego, Calif. (1989) p. 2–25; and Gatenby (1989) in Plant Biotechnology, eds. Kung, S. and Arntzen, C. J., Butterworth Publishers, Boston, Mass. p. 93–112).

The biolistic or particle gun method, which permits genetic material to be delivered directly into intact cells or tissues by bombarding regeneratable tissues, such as meristems or embryogenic callus, with DNA-coated microparticles has contributed to plant transformation simplicity and efficiency. The microparticles penetrate the plant cells and act as inert carriers of a genetic material to be introduced therein. Microprojectile bombardment of embryogenic suspension cultures has proven successful for the production of transgenic plants of a variety of species. Various parameters that influence DNA delivery by particle bombardment have been defined (Klein et al., Bio/Technology (1998) 6:559–563; McCabe et al., Bio/Technology (1998) 6:923–926; and Sanford, Physiol. Plant. (1990) 79:206–209).

Micropipette systems are also used for the delivery of foreign DNA into plants via microinjection (Neuhaus et al., Theor. Appl. Genet. (1987) 75:30–36; and Neuhaus and Spangenberg, Physiol. Plant. (1990) 79:213–217).

Other techniques developed to introduce foreign genes into plants include direct DNA uptake by plant tissue, or plant cell protoplasts (Schell and Vasil (1987) Academic Publishers, San Diego, Calif. p. 52–68; and Toriyama et al., Bio/Technology (1988) 6:1072–1074) or by germinating pollen (Chapman, Mantell and Daniels (1985) W. Longman, London, p. 197–209; and Ohta, Proc. Natl. Acad. Sci. USA (1986) 83:715–719).

DNA uptake induced by brief electric shock of plant cells has also been described (Zhang et al., Plant. Cell. Rep. (1988) 7:379–384 and Fromm et al., Nature (1986) 319:791–793).

In addition, virus mediated plant transformation has also been extensively described. Transformation of plants using plant viruses is described, for example, in U.S. Pat. No. 4,855,237 (BGV), EP-A 67,553 (TMV), Japanese Published Application No. 63-14693, EPA 194,809, EPA 278,667, and Gluzman et al., (1988) Communications in Molecular Biology: Viral Vectors, Cold Spring Harbor Laboratory, New York, pp. 172–189. Pseudovirus particles for use in expressing foreign DNA in many hosts, including plants, have also been described, for reference, see, for example WO 87/06261.

The production of recombinant proteins and peptides in plants has been investigated using a variety of approaches including transcriptional fusions using a strong constitutive plant promoter (e.g., from cauliflower mosaic virus, Sijmons et al., Bio/Technology (1990) 8:217–221); transcriptional fusions with organ specific promoter sequences (Radke et al., Theoret. Appl. Genet. (1988) 75:685–694); and translational fusions which require subsequent cleavage of a recombinant protein (Vanderkerckove et al., Bio/Technology (1989) 7:929–932).

The application of such genetic transformation techniques has allowed the incorporation of a variety of important genetic traits for crop improvement and also for the biotechnological production of extractable, valuable, foreign proteins including enzymes, vaccine proteins and antibodies.

Foreign proteins that have been successfully expressed in plant cells include proteins from bacteria (Fraley et al. Proc. Natl. Acad. Sci. U.S.A (1993) 80:4803–4807), animals (Misra and Gedamu, Theor. Appl. Genet. (1989) 78:161–168), fungi and other plant species (Fraley et al. Proc. Natl. Acad. Sci. U.S.A. (1983) 80:4803–4807). Some proteins, predominantly markers of DNA integration, have been expressed in specific cells and tissues including seeds (Sen Gupta-Gopalan et al. Proc. Natl. Acad. Sci. U.S.A. (1985) 82:3320–3324; Radke et al. Theor. Appl. Genet. (1988) 75:685–694).

Due to the advantageous economics of field-grown crops, the ability to synthesize proteins in storage organs like tubers, seeds, fruits and leaves and the ability of plants to perform many of the post-translational modifications previously described, several plant expression systems are currently investigated for potential as highly effective and economically feasible systems for the production of recombinant proteins.

Since highly expressive systems such as the ubiquitin fusion system described in U.S. Pat. No. 5,773,705 have been demonstrated, a major hurdle to an effective plant expression system resides with the relatively complicated purification procedures necessary in order to purify the recombinant protein.

As such, alternative expression approaches have been undertaken in an effort to simplify the purification procedure of the recombinant protein from the plant cells.

One such system focuses on the use of seed-storage protein promoters as a means of deriving seed-specific expression. Using such a system, Vanderkerckove et al., (Bio/Technol. (1989) 7:929–932) expressed the peptide Leu-enkephalin in seeds of *Arabidopsis thaliana* and *Brassica napus*. The level of expression of this peptide was quite low and it appeared that expression of this peptide was limited to endosperm tissue.

Another system utilizing seeds as an expression host is disclosed in U.S. Pat. No. 5,888,789. This system provides for the secretion of heterologous protein by malting of monocot plant seeds. The heterologous genes are expressed during germination of the seeds and isolated from a malt.

U.S. Pat. No. 5,580,768 describes a method of producing a genetically transformed fluid-producing plant. The genetically transformed plant which can be for example, a rubber secreting (Hevea) plant is capable of expressing the target product in the fluid that it produces which in this case is latex.

U.S. Pat No. 5,650,554 describes the use of a class of genes called oil body protein genes, that have unique features, allowing the production of recombinant proteins that can be easily separated from other host cell components.

Many additional expression systems have been described utilizing specific targeting or directing of recombinant proteins to specific plant tissues.

Although systems which target or direct recombinant protein production to specific tissues allow for easier recombinant protein isolation such systems are typically limited in the effective host range and/or the amounts of recombinant proteins produced since such systems fail to exploit the entire plant biomass.

A novel approach for simplifying the purification of recombinant enzymes from plant host cells is disclosed in U.S. Pat. No. 5,474,925 which describes an expression construct utilizing a signal peptide translationally fused to a recombinant enzyme which targets the enzyme to the cellulose matrix of the cell wall. This enables the isolation of the enzyme along with the easily recoverable cellulose matrix. This system is utilized for the localized expression of commercially important enzymes in cotton fibers. According to this system, the expressed enzymes are recovered along with the cellulosic matter of the fibers. The enzyme-cellulose matrix recovered, is directly utilized for commercial enzymatic processes.

Although this system presents a simple means with which a recombinant protein can be expressed and isolated, it is limited to the production of enzymes in cotton fibers of the cotton plant.

Furthermore, a major hurdle encountered when expressing cellulose targeted proteins within a plant is the interference of the expressed products in the natural formation of the cell wall, which typically results in growth arrest of the plant growth. Although this hurdle can be overcome by, for example, targeting the protein to specific plant tissue as is the case for U.S. Pat. No. 5,474,925, this targeting severely limits the expressing biomass and as such the quantity of the expressed protein. In addition, targeting the expression to a specific plant tissue also limits the number of plant species which can be effectively utilized for such an expression.

There is thus a widely recognized need for, and it would be highly advantageous to have, a plant expression system and method which provide high level of expression of a recombinant protein and which allow simple and effective recovery of the expressed recombinant protein devoid of the above limitations.

SUMMARY OF THE INVENTION

According to one aspect of the present invention there is provided a process of expressing a recombinant protein in a plant and of isolating the recombinant protein from the plant, the process comprising the steps of (a) providing a plant, a plant derived tissue or cultured plant cells expressing a fusion protein including the recombinant protein and a cellulose binding peptide being fused thereto, the fusion protein being compartmentalized within cells of the plant, plant derived tissue or cultured plant cells, so as to be sequestered from cell walls of the cells of the plant, plant derived tissue or cultured plant cells; (b) homogenizing the plant, plant derived tissue or cultured plant cells, so as to bring into contact the fusion protein with a cellulosic matter of the plant, plant derived tissue or cultured plant cells, to thereby effect affinity binding of the fusion protein via the cellulose binding peptide to the cellulosic matter, thereby obtaining a fusion protein cellulosic matter complex; and (c) isolating the fusion protein cellulosic matter complex.

According to further features in preferred embodiments of the invention described below, the process further comprising the steps of washing the fusion protein cellulosic matter complex, thereby removing endogenous plant proteins and other plant material therefrom and collecting the fusion protein cellulosic matter complex as a final product of the process.

According to still further features in the described preferred embodiments the process further comprising the steps of washing the fusion protein cellulosic matter complex, thereby removing endogenous plant proteins and other plant material therefrom, exposing the fusion protein cellulosic matter complex to conditions effective in dissociating the fusion protein from the cellulosic matter; and isolating the fusion protein, thereby obtaining an isolated fusion protein.

According to still further features in the described preferred embodiments the process further comprising the steps of exposing the isolated fusion protein to conditions effective in digesting the fusion protein so as to release the recombinant protein therefrom, thereby obtaining a released recombinant protein and isolating the released recombinant protein.

According to still further features in the described preferred embodiments the process further comprising the steps of washing the fusion protein cellulosic matter complex, thereby removing endogenous plant proteins and other plant material therefrom, exposing the fusion protein cellulosic matter complex to conditions effective in digesting the fusion protein so as to release the recombinant protein therefrom, thereby obtaining a released recombinant protein, and isolating the released recombinant protein.

According to still further features in the described preferred embodiments, the conditions effective in dissociating the fusion protein from the cellulosic matter are selected from the group consisting of basic conditions, denaturative conditions and affinity displacement conditions.

According to still further features in the described preferred embodiments, the conditions effective in digesting the fusion protein so as to release the recombinant protein therefrom are selected from the group consisting of proteolysis effected via a protease and proteolysis effected under predetermined cis or trans conditions for digesting a controllable intervening protein sequence.

According to another aspect of the present invention there is provided a genetically modified or viral infected plant or cultured plant cells expressing a fusion protein including a recombinant protein and a cellulose binding peptide.

According to further features in preferred embodiments of the invention described below, the fusion protein is compartmentalized within cells of the plant or cultured plant cells, so as to be sequestered from cell walls of the cells of the plant or cultured plant cells.

According to still further features in the described preferred embodiments the fusion protein is compartmentalized within a cellular compartment selected from the group consisting of cytoplasm, endoplasmic reticulum, golgi apparatus, oil bodies, starch bodies, chloroplastids, chloroplasts, chromoplastids, chromoplasts, vacuole, lysosomes, mitochondria, and nucleus.

According to still further features in the described preferred embodiments expression of the fusion protein is under a control of a constitutive or tissue specific plant promoter.

According to still further features in the described preferred embodiments the fusion protein includes a recombinant protein and a cellulose binding peptide separated therebetween via a unique amino acid sequence recognizable and digestible by a protease or under predetermined cis or trans conditions for digesting a controllable intervening protein sequence.

According to yet another aspect of the present invention there is provided a composition of matter comprising (a) a plant derived cellulosic matter; and (b) a fusion protein including a recombinant protein and a cellulose binding peptide separated therebetween via a unique amino acid sequence recognizable and digestible by a protease or under predetermined cis or trans conditions for digesting a controllable intervening protein sequence, the fusion protein being complexed to the plant derived cellulosic matter by affinity binding via the cellulose binding peptide.

According to still another aspect of the present invention there is provided a nucleic acid molecule comprising (a) a promoter sequence for directing protein expression in plant cells; (b) a heterologous nucleic acid sequence including (i) a first sequence encoding a cellulose binding peptide; (ii) a second sequence encoding a recombinant protein, wherein the first and second sequences are joined together in frame; optionally (iii) a third sequence encoding a signal peptide for directing a protein to a cellular compartment, the third sequence being upstream and in frame with the first and second sequences; and/or optionally (iv) a fourth sequence encoding a unique amino acid sequence being recognizable and digestible by a protease or under predetermined cis or trans conditions for digesting a controllable intervening protein sequence, the fourth sequence being between and in frame with the first and second sequences, wherein, the heterologous nucleic acid sequence being down stream the promoter sequence, such that expression of the heterologous nucleic acid sequence is effectable by the promoter sequence.

According to further features in preferred embodiments of the invention described below, the nucleic acid molecule further comprising a sequence element selected from the group consisting of an origin of replication for propagation in bacterial cells, at least one sequence element for integration into a plant's genome, a polyadenylation recognition sequence, a transcription termination signal, a sequence encoding a translation start site, a sequence encoding a translation stop site, plant RNA virus derived sequences, plant DNA virus derived sequences, tumor inducing (Ti) plasmid derived sequences, and a transposable element derived sequence.

The present invention successfully addresses the shortcomings of the presently known configurations by providing a novel process of expressing and isolating recombinant proteins and recombinant protein products from plants, plant derived tissue or cultured plant cells, which process exploits (i) the high affinity between cellulose binding peptides and cellulose; (ii) the inherent abundance of cellulose in planta; and (iii) the simplicity associated with cellulose isolation from plants, plant derived tissue and/or cultured plant cells.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
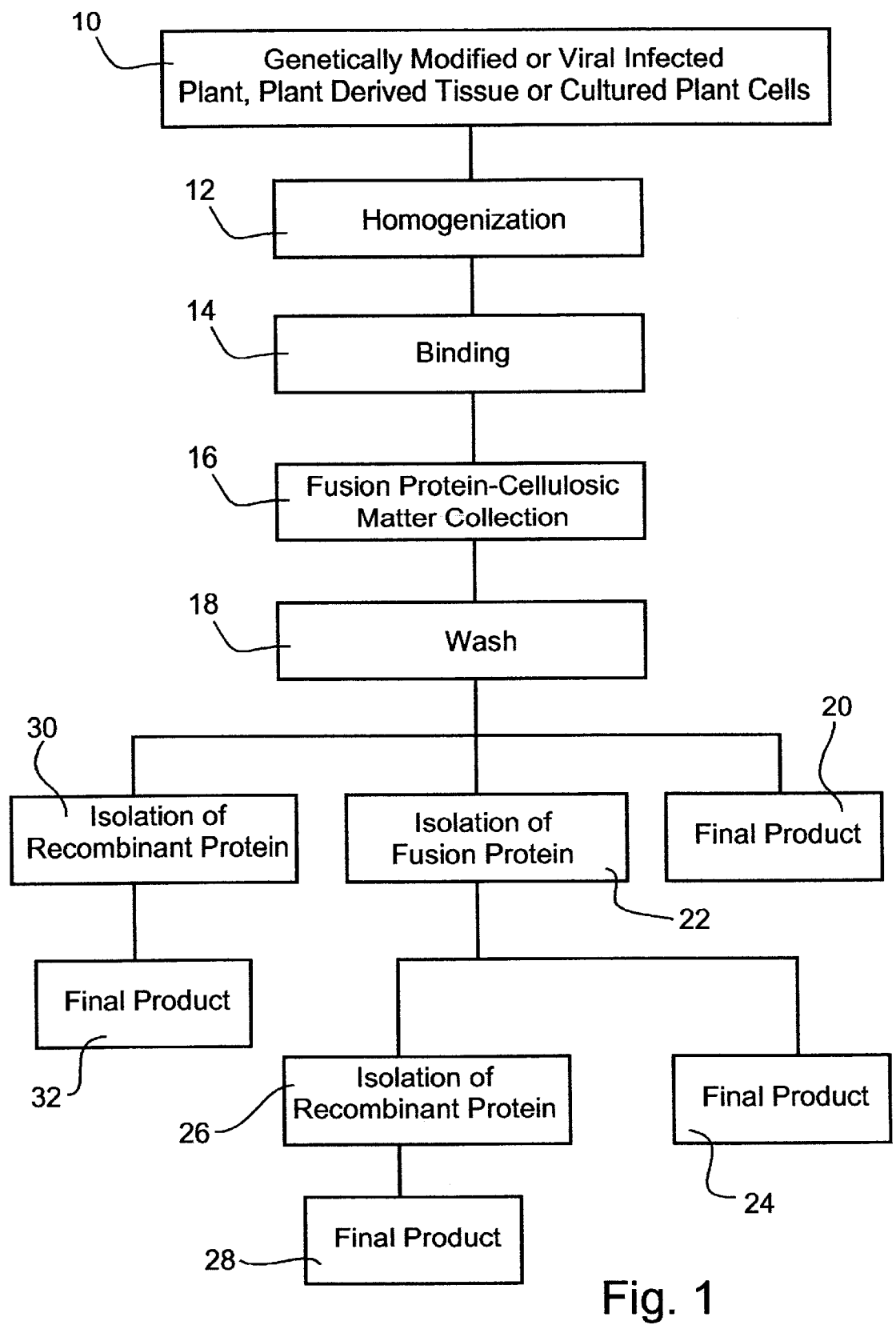
FIG. 1 is a process flow chart demonstrating the process according to the present invention.

The present invention is of a process which can be used for expressing and isolating recombinant proteins and recombinant protein products from plants, plant derived tissue or cultured plant cells. The present invention is further of nucleic acid molecules and genetically modified or viral infected plants or plant cells which are useful while implementing the process, and further of a novel composition of matter which results from the process. Specifically, the present invention can be used to obtain large quantities of the recombinant proteins and the recombinant protein products in a simple and cost effective manner, since the process according to the present invention exploits (i) the high affinity between cellulose binding peptides and cellulose; (ii) the inherent abundance of cellulose in planta; and (iii) the simplicity associated with cellulose isolation from plants, plant derived tissue and/or cultured plant cells.

The principles and operation of a process according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Process:

Referring now to the drawings, FIG. 1 is a flow chart illustrating the process according to the teachings of the present invention.

The process according to the present invention is directed at expressing a recombinant protein in a plant and further at isolating the recombinant protein from the plant. The process according to the present invention is effected by first providing a plant, a plant derived tissue or cultured plant cells (which are referred to herein below individually and collectively as "plant material") 10 expressing a fusion protein which includes the recombinant protein and a cellulose binding peptide fused thereto. The fusion protein is compartmentalized within cells of the plant material, so as to be sequestered from cell walls of the cells of the plant material. As used herein in the specification and in the claims section that follows, the phrase "cultured plant cells" includes both non-differentiated plant cell cultures and some what more differentiated callus cultures.

Compartmentalizing and thereby sequestering the fusion protein from the cell walls is an essential feature of the present invention because high levels of expressed cellulose binding peptide associated with plant cell walls inhibit plant growth to a great extent. See to this effect U.S. patent applications Ser. Nos. 09/006,632; 09/006,636; and PCT/IL98/00345 (WO 99/07830).

When sufficient expression has been detected by sampling and testing the plant material as further detailed hereinunder, the plant material is homogenized 12 so as to bring into contact the fusion protein with a cellulosic matter of the plant material, to thereby effect affinity binding 14 of the fusion protein via the cellulose binding peptide to the cellulosic matter, thereby obtaining a fusion protein cellulosic matter complex. Conditions such as, but not limited to, temperature, pH, salt concentration, time and the like are preferably set so as to allow maximal binding. Such conditions are well know to the skilled artisan and can be experimentally modified to best suit a specific application. Sampling and testing can be employed to monitor the binding process, as further detailed hereinunder.

When sufficient binding has occurred the fusion protein cellulosic matter complex is collected or isolated 16 by methods well known to the skilled artisan which method are traditionally employed for isolation of cellulosic matter from plant material. Thereafter, a wash step 18 is employed to remove unbound material, including, in particular, unbound endogenous plant proteins, thereby isolating the fusion protein cellulosic matter complex. The wash step can be repeated one or several times with a single or several wash solutions, each of which can include in addition to water, buffers, salts, detergents and the like to efficiently effect the removal of unbound matter from the fusion protein cellulosic matter complex. The wash step can be effected in solution using appropriate stiring, however, advantageously, the wash step is effected within a column into which the collected or isolated fusion protein cellulosic matter complex is packed and subsequently washed.

According to one embodiment of the present invention, and as indicated in FIG. 1 by numeral 20, the fusion protein cellulosic matter complex is collected as a final product of the process. Such a final product can serve as a pack for affinity columns. In this case the recombinant protein is selected to have affinity to a ligand, which can then be affinity purified via a column packed with the fusion protein cellulosic matter complex, in a manner otherwise similar to that described in U.S. Pat. No. 5,474,925, which is incorporated herein by reference. One of the advantages of the process described herein over the teachings of U.S. Pat. No. 5,474,925 is that by sequestering the fusion protein from the cell walls one can achieve very high expression of the fusion protein as compared to the low expression levels practically enabled by U.S. Pat. No. 5,474,925, because no deleterious effect on plant growth is exerted. As a result, the specific activity of the fusion protein cellulosic matter complex formed according to the present invention, i.e., the number of fusion protein molecules per weight of cellulosic matter, is far superior. Further details relating to the effect of high cellulose binding peptide expression on plant development see also PCT/IL98/000345.

According to another embodiment of the present invention, as indicated by numeral 22, the final product of the process according to the present invention is the fusion protein itself 24. Thus, according to this embodiment of the present invention, conditions effective in dissociating the fusion protein from the cellulosic matter are used to effect such dissociation. The dissociated fusion protein is thereafter readily isolated by any conventional separation technique, such as, but not limited to, elution or size separation, such as differential filtration or centrifugation, thereby obtaining an isolated fusion protein. Conditions effective in dissociating the fusion protein from the cellulosic matter include, but are not limited to, basic conditions (e.g., 20 mM Tris pH 12) which are known to dissociate all cellulose binding peptides from cellulose, denaturative conditions, or affinity displacement conditions, e.g., using 200 nM glucose or cellobiose which are know in their ability to elute family IX cellulose binding domains (CBDs). Alternatively, a protein cleavage site can be inserted in the cellulose binding peptide to facilitate the dissociation of the fusion protein by specific proteolysis, for example. See to this effect and to other uses of CBD-fusion proteins U.S. Pat. Nos. 5,719,044; 5,670,623; 5,856,021; 5,137,819; 5,202, 247; 5,340,731; and 5,474,925; and U.S. patent applications Ser. Nos. 08/788,621; and 08/788,622; EP 0 381 719 B1, and EP application No. 93907724.4. See also the teachings of U.S. Pat. No. 5,834,247, which is further described hereinunder.

As indicated by numeral 26, the fusion protein thus isolated can be exposed to conditions effective in digesting the fusion protein so as to release the recombinant protein therefrom, thereby obtaining a released recombinant protein which can be thereafter isolated as a final product 28. Conditions effective in digesting the fusion protein so as to release the recombinant protein therefrom include, but are not limited to, proteolysis effected via a protease, such as, but not limited to, Factor Xa, enterokinase, thrombin, trypsin, papain, pepsin, chemotrypsin and the like, or proteolysis effected via controllable intervening protein sequence (CIVPS) inserted into or adjacent the cellulose binding peptide, the CIVPS are capable of excision from or cleavage of the peptide under predetermined conditions in cis or in trans, e.g., increase in temperature, exposure to light, unblocking of amino acid residues by dephosphorylation and treatment with chemical reagents or deglycosylation, examples include proteolysis effected under acidic conditions (HCl, e.g., to cleave between Asp and Pro) and proteolysis effected by a proteolysing reagent, such as CNBr to cleave downstream of Met, all as known in the art and/or as further described in U.S. Pat. No. 5,834, 247, which is incorporated herein by reference.

Isolating final product 28 from other proteolytic products derived, for example, from the cellulose binding peptide, can be effected by any one of a number of protein isolation techniques well known to the skilled artisan, including, but not limited to, affinity separation via, for example, antibodies bound to a solid support, size and/or charge based separation via gel electrophoresis or chromatography, and the like. Additional methods include, but are not limited to, fractionation, gel-filtration, ion-exchange, hydrophobic, and affinity chromatography, ultrafiltration and crystallization.

According to an alternative embodiment of the process of the present invention, as indicated in FIG. 1 by numeral 30, the washed fusion protein cellulose matter complex resulting from step 18 is exposed to conditions effective in digesting the fusion protein so as to release the recombinant protein therefrom, thereby obtaining a released recombinant protein. These conditions are similar to those described with respect to step 26. The released recombinant protein is thereafter readily isolated by any conventional separation technique, such as, but not limited to, displacement or size separation, such as differential filtration or centrifugation, thereby obtaining an isolated recombinant protein final product 32.

Cellulose binding peptides:

As used herein in the specification and in the claims section below, the phrase "cellulose binding peptide" includes peptides e.g., proteins and domains (portions) thereof, which are capable of, when expressed in plant cells, affinity binding to a plant derived cellulosic matter following homogenization and cell rupture. The phrase thus includes, for example, peptides which were screened for their cellulose binding activity out of a library, such as a peptide library or a DNA library (e.g., a cDNA expression library or a display library) and the genes encoding such peptides isolated and are expressible in plants. Yet, the phrase also includes peptides designed and engineered to be capable of binding to cellulose and/or units thereof.

Such peptides include amino acid sequences expressible in plants that are originally derived from a cellulose binding region of, e.g., a cellulose binding protein (CBP) or a cellulose binding domain (CBD). The cellulose binding peptide according to the present invention can include any amino acid sequence expressible in plants which binds to a cellulose polymer. For example, the cellulose binding domain or protein can be derived from a cellulase, a binding domain of a cellulose binding protein or a protein screened for, and isolated from, a peptide library, or a protein designed and engineered to be capable of binding to cellulose or to saccharide units thereof, and which is expressible in plants. The cellulose binding domain or protein can be naturally occurring or synthetic, as long as it is expressible in plants. Suitable polysaccharidases from which a cellulose binding domain or protein expressible in plants may be obtained include β-1,4-glucanases. In a preferred embodiment, a cellulose binding domain or protein from a cellulase or scaffoldin is used. Typically, the amino acid sequence of the cellulose binding peptide expressed in plants according to the present invention is essentially lacking in the hydrolytic activity of a polysaccharidase (e.g., cellulase, chitinase), but retains the cellulose binding activity. The amino acid sequence preferably has less than about 10% of the hydrolytic activity of the native polysaccharidase; more preferably less than about 5%, and most preferably less than about 1% of the hydrolytic activity of the native polysaccharidase, ideally no activity altogether.

The cellulose binding domain or protein can be obtained from a variety of sources, including enzymes and other proteins which bind to cellulose which find use in the subject invention.

In Table 4 below are listed those binding domains which bind to one or more soluble/insoluble polysaccharides including all binding domains with affinity for soluble glucans (α, β, and/or mixed linkages). The N1 cellulose-binding domain from endoglucanase CenC of *C. fimi* is the only protein known to bind soluble cellosaccharides and one of a small set of proteins which are known to bind any soluble polysaccharides. Also, listed in Tables 1 to 3 are examples of proteins containing putative β-1,3-glucan-binding domains (Table 1); proteins containing Streptococcal glucan-binding repeats (Cp1 superfamily) (Table 2); and enzymes with chitin-binding domains, which may also bind cellulose (Table 3). The genes encoding each one of the peptides listed in Tables 1–4 are either isolated or can be isolated as further detailed hereinunder, and therefore, such peptides are expressible in plants. Scaffoldin proteins or portions thereof, which include a cellulose binding domain, such as that produced by *Clostridium cellulovorans* (Shoseyov et al., PCT/US94/04132) can also be used as the cellulose binding peptide expressible in plants according to the present invention. Several fungi, including Trichoderma species and others, also produce polysaccharidases from which polysaccharide binding domains or proteins expressible in plants can be isolated. Additional examples can be found in, for example, Microbial Hydrolysis of Polysaccharides, R. A. J. Warren, Annu. Rev. Microbiol. 1996, 50:183–212; and "Advances in Microbial Physiology" R. K. Poole, Ed., 1995, Academic Press Limited, both are incorporated by reference as if fully set forth herein.

TABLE 1

Overview of proteins containing putative β-1,3 glucan-binding domains

| Source (strain) | Protein | accession No. | Ref[1] |
|---|---|---|---|
| Type I | | | |
| B. circulans (WL-12) | GLCA1 | P23903/M34503/JQ0420 | 1 |
| B. circulans (IAM 1165) | BglH | JN0772/D17519/S67033 | 2 |
| Type II | | | |
| Actinomadura sp. (FC7) | XynII | U08894 | 3 |
| Arthrobacter sp. (YCWD3) | GLCI | D23668 | 9 |
| O. xanthineolytica | GLC | P22222/M60826/A39094 | 4 |
| R. faecitabidus (YLM-50) | RP I | Q05308/A45053/D10753 | 5a, b |
| R. communis | Ricin | A12892 | 6 |
| S. lividans (1326) | XlnA | P26514/M64551/JS07986 | 7 |
| T. tridentatus | FactorGa | D16622 | 8 |

B.: *Bacillus*, O.: *Oerskovia*, R. *faecitabidus*: *Rarobacter faecitabidus*, R. *communis*: *Ricinus communis*, S.: *Streptomyces*, T.: *Tachypleus* (Horseshoe Crab)

[1]References:
1) Yahata et al. (1990) Gene 86, 113–117
2) Yamamoto et al. (1993) Biosci. Biotechnol. Biochem. 57, 1518–1525
3) Harpin et al. (1994) EMBL Data Library
4) Shen et al. (1991) J. Biol. Chem. 266, 1058–1063
5a) Shimoi et al. (1992) J. Biol. Chem. 267, 25189–25195
5b) Shimoi et al. (1992) J. Biochem 110, 608–613
6) Horn et al. (1989) Patent A12892
7) Shareck et al. (1991) Gene 107, 75–92
8) Seki et al. (1994) J. Biol. Chem. 269, 1370–1374
9) Watanabe et al. (1993) EMBL Data Library

TABLE 2

Overview of proteins containing Streptococcal glucan-binding repeats (Cp1 superfamily)

| Source | Protein | Accession No. | Ref.[2] |
|---|---|---|---|
| S. downei (sobrinus) (0MZ176) | GTF-I | D13858 | 1 |
| S. downei (sobrinus) (MFe28) | GTF-I | P11001/M17391 | 2 |
| S. downei (sobrinus) (MFe28) | GTF-S | P29336/M30943/A41483 | 3 |
| S. downei (sobrinus) (6715) | GTF-I | P27470/D90216/A38175 | 4 |
| S. downei (sobrinus) | DEI | L34406 | 5 |
| S. mutants (Ingbritt) | GBP | M30945/A37184 | 6 |
| S. mutants (GS-5) | GTF-B | A33128 | 7 |
| S. mutants (GS-5) | GTF-B | P08987/M17361/B33135 | 8 |
| S. mutants | GTF-B[3'-ORF] | P05427/C33135 | 8 |
| S. mutants (GS-5) | GTF-C | P13470/M17361/M22054 | 9 |
| S. mutants (GS-5) | GTF-C | not available | 10 |
| S. mutants (GS-5) | GTF-D | M29296/A45866 | 11 |
| S. salivarius | GTF-J | A44811/S22726/S28809 Z11873/M64111 | 12 |
| S. salivarius | GTF-K | S22737/S22727/Z11872 | 13 |
| S. salivarius (ATCC25975) | GTF-L | L35495 | 14 |
| S. salivarius (ATCC25975) | GTF-M | L35928 | 14 |
| S. pneumoniae R6 | LytA | P06653/A25634/M13812 | 15 |
| S. pneumoniae | PspA | A41971/M74122 | 16 |
| Phage HB-3 | HBL | P32762/M34652 | 17 |
| Phage Cp-1 | CPL-1 | P15057/J03586/A31086 | 18 |
| Phage Cp-9 | CPL-9 | P19386/M34780/JQ0438 | 19 |
| Phage EJ-1 | EJL | A42936 | 20 |
| C. difficile (VPI 10463) | ToxA | P16154/A37052/M30307 X51797/S08638 | 21 |
| C. difficile (BARTS W1) | ToxA | A60991/X17194 | 22 |
| C. difficile (VPI 10463) | ToxB | P18177/X53138/X60984 S10317 | 23, 24 |
| C. difficile (1470) | ToxB | S44271/Z23277 | 25, 26 |
| C. novyi | a-toxin | S44272/Z23280 | 27 |
| C. novyi | a-toxin | Z48636 | 28 |
| C. acetobutylicum (NCIB8052) | CspA | S49255/Z37723 | 29 |
| C. acetobutylicum | CspB | Z50008 | 30 |

TABLE 2-continued

Overview of proteins containing Streptococcal glucan-binding repeats (Cpl superfamily)

| Source | Protein | Accession No. | Ref.[2] |
|---|---|---|---|
| (NCIB8052) | | | |
| C. acetobutylicum | CspC | Z50033 | 30 |
| (NCIB8052) | | | |
| C. acetobutylicum | CspD | Z50009 | 30 |
| (NCIB8052) | | | |

[2]References:
1) Sato et al. (1993) DNA sequence 4, 19–27
2) Ferreti et al. (1987) J. Bacteriol. 169, 4271–4278
3) Gilmore et al. (1990) J. Infect. Immun. 58, 2452–2458
4) Abo et al. (1991) J. Bacteriol. 173, 989–996
5) Sun et al. (1994) J. Bacteriol. 176, 7213–7222
6) Banas et al. (1990) J. Infect. Immun. 58, 667–673
7) Shiroza et al. (1990) Protein Sequence Database
8) Shiroza et al. (1987) J. Bacteriol. 169, 4263–4270
9) Ueda et al. (1988) Gene 69, 101–109
10) Russel (1990) Arch. Oral. Biol. 35, 53–58
11) Honda et al. (1990) J. Gen. Microbiol. 136, 2099–2105
12) Giffard et al. (1991) J. Gen. Microbiol. 137, 2577–2593
13) Jacques (1992) EMBL Data Library
14) Simpson et al. (1995) J. Infect. Immun. 63, 609–621
15) Gargia et al. (1986) Gene 43, 265–272
16) Yother et al. (1992) J. Bacteriol. 174, 601–609
17) Romero et al. (1990) J. Bacteriol. 172, 5064–5070
18) Garcia et al. (1988) Proc. Natl. Acad. Sci, USA 95, 914–918
19) Garcia et al. (1990) Gene 86, 81–88
20) Diaz et al. (1992) J. Bacteriol. 174, 5516–5525
21) Dove et al. (1990) J. Infect. Immun. 58, 480–488
22) Wren et al. (1990) FEMS Microbiol. Lett. 70, 1–6
23) Barroso et a. (1990) Nucleic Acids Res. 18, 4004–4004
24) von Eichel-Streiber et al. (1992) Mol. Gen. Genet. 233, 260–268
25) Sartinger et al. (1993) EMBL Data Library
26) von Eichel-Streiber et al. (1995) Mol. Microbiol. In Press
27) Hofmann et al. (1993) EMBL Data Library
28) Hofmann et al. (1995) Mol. Gen. Genet. In Press
29) Sanchez et al. (1994) EMBL Data Library
30) Sanchez et al. (1995) EMBL Data Library New cellulose binding peptides with interesting binding characteristics and specificities can be identified and screened for and the genes encoding same isolated using well known molecular biology approaches combined with a variety of other procedures including, for example, spectroscopic (titration) methods such as: NMR spectroscopy (Zhu et al. Biochemistry (1995) 34:13196–13202, Gehring et al. Biochemistry (1991) 30:5524–5531), UV difference spectroscopy (Belshaw et al. Eur. J. Biochem. (1993) 211:717–724), fluorescence (titration) spectroscopy (Miller et al. J. Biol. Chem. (1983) 258:13665–13672), UV or fluorescence stopped flow analysis (De Boeck et al. Eur. J. Biochem. (1985) 149:141–415), affinity methods such as affinity electrophoresis (Mimura et al. J. chromatography (1992) 597:345–350) or affinity chromatography on immobilized mono or oligosaccharides, precipitation or agglutination analysis including turbidimetric or nephelometric analysis (Knibbs et al. J. Biol. Chem. (1993) 14940–14947), competitive inhibition assays (with or without quantitative IC50 determination) and various physical or physicochemical methods including differential scanning or isothermal titration calorimetry (Sigurskjold et al. *J. Biol. Chem.* (1992) 267:8371–8376; Sigurskjold et al. Eur. J. Biol. (1994) 225:133–141) or comparative protein stability assays (melts) in the absence or presence of oligo saccharides using thermal CD or fluorescence spectroscopy.

The $K_a$ for binding of the cellulose binding domains or proteins to cellulose is at least in the range of weak antibody-antigen extractions, i.e., $\geq 10^3$, preferably $10^4$, most preferably $10^6$ M$^{-1}$. If the binding of the cellulose binding domain or protein to cellulose is exothermic or endothermic, then binding will increase or decrease, respectively, at lower temperatures, providing a means for temperature modulation of the binding step, see numeral 14 in FIG. 1.

TABLE 3

Overview of enzymes with chitin-binding domains

| Source (strain) | Enzyme | Accession No. | Ref.[3] |
|---|---|---|---|
| Bacterial enzymes | | | |
| Type I | | | |
| Aeromonas sp. (No10S-24) | Chi | D31818 | 1 |
| Bacillus circulans (WL-12) | ChiA1 | P20533/M57601/A38368 | 2 |
| Bacillus circulans (WL-12) | ChiD | P27050/D10594 | 3 |
| Janthinobacterium lividum | Chi69 | U07025 | 4 |
| Streptomyces griseus | Protease C | A53669 | 5 |
| Type II | | | |
| Aeromonas cavia (K1) | Chi | U09139 | 6 |
| Alteromonas sp (0-7) | Chi85 | A40633/P32823/D13762 | 7 |
| Autographa californica (C6) | NPH-128[a] | P41684/L22858 | 8 |
| Serratia marcescens | ChiA | A25090/X03657/L01455/P07254 | 9 |
| Type III | | | |
| Rhizopus oligosporus (IFO8631) | Chi1 | P29026/A47022/D10157/S27418 | 10 |
| Rhizopus oligosporus (IFO8631) | Chi2 | P29027/B47022/D10158/S27419 | 10 |
| Saccharomyces cerevisiae | Chi | S50371/U17243 | 11 |
| Saccharomyces cerevisiae (DBY939) | Chi1 | P29028/M74069 | 12 |
| Saccharomyces cerevisiae (DBY918) | Chi2 | P29029/M7407/B41035 | 12 |
| Plant enzymes | | | |
| Hevein superfamily | | | |
| Allium sativum | Chi | M94105 | 13 |
| Amaranthus caudatus | AMP-1[b] | P27275/A40240 | 14, 15 |
| Amaranthus caudatus | AMP-2[b] | S37381/A40240 | 14, 15 |
| Arabidopsis thaliana (cv. colombia) | ChiB | P19171/M38240/B45511 | 16 |
| Arabidopsis thaliana | PHP[c] | U01880 | 17 |
| Brassica napus | Chi | U21848 | 18 |
| Brassica napus | Chi2 | Q09023/M95835 | 19 |
| Hevea brasiliensis | Hev1[d] | P02877/M36986/A03770/A38288 | 20, 21 |
| Hordeum vulgare | Chi33 | L34211 | 22 |
| Lycopersicon esculentum | Chi9 | Q05538/Z15140/S37344 | 23 |
| Nicotiana tabacum | CBP20[e] | S72424 | 24 |
| Nicotiana tabacum | Chi | A21091 | 25 |
| Nicotiana tabacum (cv. Havana) | Chi | A29074/M15173/S20981/S19855 | 26 |
| Nicotiana tabacum (FB7-1) | Chi | JQ0993/S0828 | 27 |
| Nicotiana tabacum (cv. Samsun) | Chi | A16119 | 28 |
| Nicotiana tabacum (cv. Havana) | Chi | P08252/X16939/S08627 | 27 |
| Nicotiana tabacum (cv. BY4) | Chi | P24091/X51599/X64519/S13322 | 26, 27, 29 |
| Nicotiana tabacum (cv. Havana) | Chi | P29059/X64518/S20982 | 26 |
| Oryza sativum (IR36) | ChiA | L37289 | 30 |
| Oryza sativum | ChiB | JC2253/S42829/Z29962 | 31 |
| Oryza sativum | Chi | S39979/S40414/X56787 | 32 |
| Oryza sativum (cv. Japonicum) | Chi | X56063 | 33 |
| Oryza sativum (cv. Japonicum) | Chi1 | P24626/X54367/S14948 | 34 |
| Oryza sativum | Chi2 | P25765/S15997 | 35 |
| Oryza sativum | Chi3 | D16223 | |

TABLE 3-continued

Overview of enzymes with chitin-binding domains

| Source (strain) | Enzyme | Accession No. | Ref.[3] |
|---|---|---|---|
| (cv. Japonicum) | | | |
| *Oryza sativum* | ChiA | JC2252/S42828 | 30 |
| *Oryza sativum* | Chi1 | D16221 | 32 |
| *Oryza sativum* (IR58) | Chi | U02286 | 36 |
| *Oryza sativum* | Chi | X87109 | 37 |
| *Pisum sativum* | Chi | P36907/X63899 | 38 |
| (cv. Birte) | | | |
| *Pisum sativum* | Chi2 | L37876 | 39 |
| (cv. Alcan) | | | |
| *Populus trichocarpa* | Chi | S18750/S18751/X59995/P29032 | 40 |
| *Populus trichocarpa* (H11-11) | Chi | U01660 | 41 |
| *Phaseolus vulgaris* (cv. Saxa) | Chi | A24215/S43926/Jq0965/P36361 | 42 |
| *Phaseolus vulgaris* (cv. Saxa) | Chi | P06215/M13968/M19052/A25898 | 43, 44, 45 |
| *Sambucus nigra* | PR-3[f] | Z46948 | 46 |
| *Secale cereale* | Chi | JC2071 | 47 |
| *Solanum tuberosum* | ChiB1 | U02605 | 48 |
| *Solanum tuberosum* | ChiB2 | U02606 | 48 |
| *Solanum tuberosum* | ChiB3 | U02607/S43317 | 48 |
| *Solanum tuberosum* | ChiB4 | U02608 | 48 |
| *Solanum tuberosum* (cv. Maris Piper) | WIN-1[g] | P09761/X13497/S04926 | 49 |
| *Solanum tuberosum* (cv. Maris Piper) | WIN-2[g] | P09762/X13497/S04927 | 49 |
| *Triticum aestivum* | Chi | S38670/X76041 | 50 |
| *Triticum aestivum* | WGA-1$_h$[h] | P10968/M25536/S09623/S07289 | 51, 52 |
| *Triticum aestivum* | WGA-2$_h$ | P02876/M25537/S09624 | 51, 53 |
| *Triticum aestivum* | WA-3 | P10969/J02961/S10045/A28401 | 54 |
| *Ulmus americana* (NPS3-487) | Chi | L22032 | 55 |
| *Urtica dioica* | AGL[i] | M87302 | 56 |
| *Vigna unguiculata* (cv. Red caloona) | Chi1 | X88800 | 57 |

[a]NHP: nuclear polyhedrosis virus endochitinase like sequence; Chi: chitinase,
[b]anti-microbial peptide,
[c]pre-hevein like protein,
[d]hevein,
[e]chitin-binding protein,
[f]pathogenesis related protein,
[g]wound-induced protein,
[h]wheat germ agglutinin,
[i]agglutinin (lectin).
[3]References:
1) Udea et al. (1994) J. Ferment. Bioeng. 78, 205–211
2) Watanabe et al. (1990) J. Biol. Chem. 265, 15659–16565
3) Watanabe et al. (1992) J. Bacteriol. 174, 408–414
4) Gleave et al. (1994) EMBL Data Library
5) Sidhu et al. (1994) J. Biol. Chem. 269, 20167–20171
6) Jones et al. (1986) EMBO J. 5, 467–473
7) Sitrit et al. (1994) EMBL Data Library
8) Genbank entry only
9) Tsujibo et al. (1993) J. Bacteriol. 175, 176–181
10) Yanai et al. (1992) J. Bacteriol. 174, 7398–7406
11) Pauley (1994) EMBL Data Library
12) Kuranda et al. (1991) J. Biol. Chem. 266, 19758–19767
13) van Damme et al. (1992) EMBL Data Library
14) Broekaert et al. (1992) Biochemistry 31, 4308–4314
15) de Bolle et al. (1993) Plant Mol. Physiol. 22, 1187–1190
16) Samac et al. (1990) Plant Physiol. 93, 907–914
17) Potter et al. (1993) Mol. Plant Microbe Interact. 6, 680–685
18) Buchanan-Wollaston (1995) EMBL Data Library
19) Hamel et al. (1993) Plant Physiol. 101, 1403–1403
20) Broekaert et al. (1990) Proc. Natl. Acad. Sci. USA 87, 7633–7637
21) Lee et al. (1991) J. Biol. Chem. 266, 15944–15948
22) Leah et al. (1994) Plant Physiol. 6, 579–589
23) Danhash et al. (1993) Plant Mol. Biol. 22, 1017–1029
24) Ponstein et al. (1994) Plant Physiol. 104, 109–118
25) Meins et al. (1991) Patent EP0418695-A1
26) van Buuren et al. (1992) Mol. Gen. Genet. 232, 460–469
27) Shinshi et al. (1990) Plant Mol. Biol. 14, 357–368
28) Cornellisen et al. (1991) Patent EP0440304-A2
29) Fukuda et al. (1991) Plant Mol. Biol. 16, 1–10
30) Yun et al. (1994) EMBL Data Library
31) Kim et al. (1994) Biosci. Biotechnol. Biochem. 58, 1164–1166
32) Nishizawa et al. (1993) Mol. Gen. Genet. 241, 1–10
33) Nishizawa et al. (1991) Plant Sci 76, 211–218
34) Huang et al. (1991) Plant Mol. Biol. 16, 479–480
35) Zhu et al. (1991) Mil. Gen. Genet. 226, 289–296
36) Muthukrishnan et al. (1993) EMBL Data Library
37) Xu (1995) EMBL Data Library
38) Vad et al. (1993) Plant Sci 92, 69–79
39) Chang et al. (1994) EMBL Data Library
40) Davis et al. (1991) Plant Mol. Biol. 17, 631–639
41) Clarke et al. (1994) Plant Mol. Biol. 25, 799–815
42) Broglie et al. (1989) Plant Cell 1, 599–607
43) Broglie et al. (1986) Proc. Natl. acad. Sci. USA 83, 6820–6824
44) Lucas et al. (1985) FEBS Lett. 193, 208–210
45) Hedrick et al. (1988) Plant Physiol. 86, 182–186
46) Roberts et al. (1994) EMBL Data Library1
47) Vamagami et al. (1994) Biosci. Biotechnol. Biochem. 58, 322–329
48) Beerhues et al. (1994) Plant Mol. Biol. 24, 353–367
49) Stanford et al. (1989) Mol. Gen. Genet. 215, 200–208
50) Liao et al. (1993) EMBL Data Library
51) Smith et al. (1989) Plant Mol. Biol. 13, 601–603
52) Wright et al. (1989) J. Mol. Evol. 28, 327–336
53) Wright et al. (1984) Biochemistry 23, 280–287
54) Raikhel et al. (1987) Proc. Natl. acad. Sci. USA 84, 6745–6749
55) Hajela et al. (1993) EMBL Data Library
56) Lerner et al. (1992) J. Biol. Chem. 267, 11085–11091
57) Vo et al. (1995) EMBL Data Library

TABLE 4

Sources of polysaccharide binding domains

| Binding Domain | Proteins Where Binding Domain is Found |
|---|---|
| Cellulose Binding Domains[1] | β-glucanases (avicelases, CMCases, cellodextrinases) |
| | exoglucanses or cellobiohydrolases |
| | cellulose binding proteins |
| | xylanases |
| | mixed xylanases/glucanases |
| | esterases |
| | chitinases |
| | β-1,3-glucanases |
| | β-1,3-(β-1,4)-glucanases |
| | (β-)mannanases |
| | β-glucosidases/galactosidases |
| | cellulose synthases (unconfirmed) |
| Starch/Maltodextrin Binding Domains | α-amylases[2,3] |
| | β-amylases[4,5] |
| | pullulanases |
| | glucoamylases[6,7] |
| | cyclodextrin glucotransferases[8–10] (cyclomaltodextrin glucanotransferases) |
| | maltodextrin binding proteins[11] |
| Dextran Binding Domains | (Streptococcal) glycosyl transferases[12] |
| | dextran sucrases (unconfirmed) |
| | Clostridial toxins[13,14] |
| | glucoamylases[6] |
| | dextran binding proteins |
| β-Glucan Binding Domains | β-1,3-glucanases[15,16] |
| | β01,3-(β-1,4)-glucanases (unconfirmed) |
| | β-1,3-glucan binding protein[17] |

TABLE 4-continued

Sources of polysaccharide binding domains

| Binding Domain | Proteins Where Binding Domain is Found |
|---|---|
| Chitin Binding Domains | chitinases<br>chitobiases<br>chitin binding proteins<br>(see also cellulose binding domains)<br>Heivein |

[1]Gilkes et al., Adv. Microbiol Reviews, (1991) 303–315.
[2]S?gaard et al., J. Biol. Chem. (1993) 268:22480.
[3]Weselake et al., Cereal Chem. (1983) 60:98.
[4]Svensson et al., J. (1989) 264:309.
[5]Jespersen et al., J. (1991) 280:51.
[6]Belshaw et al., Eur. J. Biochem. (1993) 211:717.
[7]Sigurskjold et al., Eur. J. Biochem. (1994) 225:133.
[8]Villette et al., Biotechnol. Appl. Biochem. (1992) 16:57.
[9]Fukada et al., Biosci. Biotechnol. Biochem. (1992) 56:556.
[10]Lawson et al., J. Mol. Biol. (1994) 236:590.
[14]von Eichel-Streiber et al., Mol. Gen. Genet. (1992) 233:260.
[15]Klebl et al., J. Bacteriol. (1989) 171:6259.
[16]Watanabe et al., J. Bacteriol. (1992) 174:186.
[17]Duvic et al., J. Biol. Chem. (1990) :9327.

Thus, and as already stated, the phrase "polysaccharide binding peptide" includes an amino acid sequence which comprises at least a functional portion of a polysaccharide binding region (domain) of a polysaccharidase or a polysaccharide binding protein. The phrase further relates to a polypeptide screened for its cellulose binding activity out of a library, such as a peptide library or a DNA library (e.g., a cDNA library or a display library). By "functional portion" is intended an amino acid sequence which binds to cellulose.

The techniques used in isolating polysaccharidase genes, such as cellulase genes, and genes for cellulose binding proteins are known in the art, including synthesis, isolation from genomic DNA, preparation from cDNA, or combinations thereof. (See, U.S. Pat. Nos. 5,137,819; 5,202,247; 5,340,731; 5,496,934; and 5,837,814). The sequences for several binding domains, which bind to soluble oligosaccharides are known (See, FIG. 1 of PCT/CA97/00033, WO 97/26358). The DNAs coding for a variety of polysaccharidases and polysaccharide binding proteins are also known. Various techniques for manipulation of genes are well known, and include restriction, digestion, resection, ligation, in vitro mutagenesis, primer repair, employing linkers and adapters, and the like (see Sambrook et al., Molecular Cloning—A Laboratory Manual, Cold Spring Harbor Laboratory, Cold Spring Harbor, N.Y., 1989, which is incorporated herein by reference).

The amino acid sequence of a polysaccharidase can be used to design a probe to screen a cDNA or a genomic library prepared from mRNA or DNA from cells of interest as donor cells for a polysaccharidase gene or a polysaccharide binding protein gene. By using the polysaccharidase cDNA or binding protein cDNA or a fragment thereof as a hybridization probe, structurally related genes found in other species can be easily cloned and provide a cellulose binding peptide which is expressible in plants according to the present invention. Particularly contemplated is the isolation of genes from organisms that express polysaccharidase activity using oligonucleotide probes based on the nucleotide sequences of genes obtainable from an organism wherein the catalytic and binding domains of the polysaccharidase are discrete, although other polysaccharide binding proteins also can be used (see, for example, Shoseyov, et al., Proc. Nat'l. Acad. Sci. (USA) (1992) 89:3483–3487).

Probes developed using consensus sequences for the binding domain of a polysaccharidase or polysaccharide-binding protein are of particular interest. The β-1,4-glycanases from C. fimi characterized to date are endoglucanases A, B, C and D (CenA, CenB, CenC and CenD, respectively), exocellobiohydrolases A and B (CbhA and CbhB, respectively), and xylanases A and D (Cex and XylD, respectively) (see Wong et al. (1986) Gene, 44:315; Meinke et al. (1991) J. Bacteriol., 173:308; Coutinho et al., (1991) Mol. Microbiol. 5:1221; Meinke et al., (1993) Bacteriol., 175:1910; Meinke et al., (1994) Mol. Microbiol., 12:413; Shen et al., Biochem. J., in press; O'Neill et al., (1986) Gene, 44:325; and Millward-Sadler et al., (1994) Mol. Microbiol., 11:375). All are modular proteins of varying degrees of complexity, but with two features in common: a catalytic domain (CD) and a cellulose-binding domain (CBD) which can function independently (see Millward-Sadler et al., (1994) Mol. Microbiol., 11:375; Gilkes et al., (1988) J. Biol. Chem., 263:10401; Meinke et al., (1991) J. Bacteriol., 173:7126; and Coutinho et al., (1992) Mol. Microbiol., 6:1242). In four of the enzymes, CenB, CenD, CbhA and CbhB, fibronectin type III (Fn3) repeats separate the N-terminal CD from the C-terminal CBD. The CDs of the enzymes come from six of the families of glycoside hydrolases (see Henrissat (1991) Biochem. J., 280:309; and Henrissat et al., (1993) Biochem. J., 293:781); all of the enzymes have an N- or C-terminal CBD or CBDs (see Tomme et al., Adv. Microb. Physiol., in press); CenC has tandem CBDs from family IV at its N-terminus; CenB and XylD each have a second, internal CBD from families III and II, respectively. Cex and XylD are clearly xylanases; however, Cex, but not XylD, has low activity on cellulose. Nonetheless, like several other bacterial xylanases (see Gilbert et al., (1993) J. Gen. Microbiol., 139:187), they have CBDs. C. fimi probably produces other β-1,4-glycanases. Similar systems are produced by related bacteria (see Wilson (1992) Crit. Rev. Biotechnol., 12:45; and Hazlewood et al., (1992) J. Appl. Bacteriol., 72:244). Unrelated bacteria also produce glycanases; Clostridium thermocellum, for example, produces twenty or more β-1,4-glycanases (see Beguin et al., (1992) FEMS Microbiol. Lett., 100:523). The CBD derived from C. fimi endoglucanase C N1, is the only protein known to bind soluble cellosaccharides and one of a small set of proteins that are known to bind any soluble polysaccharides.

Examples of suitable binding domains are shown in FIG. 1 of PCT/CA97/00033 (WO 97/26358), which presents an alignment of binding domains from various enzymes that bind to polysaccharides and identifies amino acid residues that are conserved among most or all of the enzymes. This information can be used to derive a suitable oligonucleotide probe using methods known to those of skill in the art. The probes can be considerably shorter than the entire sequence but should at least be 10, preferably at least 14, nucleotides in length. Longer oligonucleotides are useful, up to the full legnth of the gene, preferably no more than 500, more preferably no more than 250, nucleotides in length. RNA or DNA probes can be used. In use, the probes are typically labeled in a detectable manner, for example, with $^{32}P$, $^3H$, biotin, avidin or other detectable reagents, and are incubated with single-stranded DNA or RNA from the organism in which a gene is being sought. Hybridization is detected by means of the label after the unhybridized probe has been separated from the hybridized probe. The hybridized probe is typically immobilized on a solid matrix such as nitrocellulose paper. Hybridization techniques suitable for use with oligonucleotides are well known to those skilled in the art.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

Generally, the binding domains identified by probing nucleic acids from an organism of interest will show at least about 40% identity (including as appropriate allowances for conservative substitutions, gaps for better alignment and the like) to the binding region or regions from which the probe was derived and will bind to a soluble β-1,4 glucan with a $K_a$ of $\geq 10^3$ $M^{-1}$. More preferably, the binding domains will be at least about 60% identical, and most preferably at least about 70% identical to the binding region used to derive the probe. The percentage of identity will be greater among those amino acids that are conserved among polysaccharidase binding domains. Analyses of amino acid sequence comparisons can be performed using programs in PC/Gene (IntelliGenetics, Inc.). PCLUSTAL can be used for multiple sequence alignment and generation of phylogenetic trees.

In order to isolate the polysaccharide binding protein or a polysaccharide binding domain from an enzyme or a cluster of enzymes that binds to a polysaccharide, several genetic approaches can be used. One method uses restriction enzymes to remove a portion of the gene that codes for portions of the protein other than the binding portion thereof. The remaining gene fragments are fused with expression control sequences to obtain a mutated gene that encodes a truncated protein. Another method involves the use of exonucleases such as Bal31 to systematically delete nucleotides either externally from the 5' and the 3' ends of the DNA or internally from a restricted gap within the gene. These gene deletion methods result in a mutated gene encoding a shortened protein molecule which can then be evaluated for substrate or polysaccharide binding ability.

Any cellulose binding protein or cellulose binding domain may be used in the present invention. The term "cellulose binding protein" ("CBP") refers to any protein or polypeptide which specifically binds to cellulose. The cellulose binding protein may or may not have cellulose or cellulolytic activity. The term "cellulose binding domain" ("CBD") refers to any protein or polypeptide which is a region or portion of a larger protein, said region or portion binds specifically to cellulose. The cellulose binding domain (CBD) may be a part or portion of a cellulase, xylanase or other polysaccharidase, e.g., a chitinase, etc., a sugar binding protein such as maltose binding protein, or scaffoldin such as CbpA of *Clostridium celluvorans*, etc. Many cellulases and hemicellulases (e.g. xylanases and mannases) have the ability to associate with cellulose. These enzymes typically have a catalytic domain containing the active site for substrate hydrolysis and a carbohydrate-binding domain or cellulose-binding domain for binding cellulose. The CBD may also be from a non-catalytic polysaccharide binding protein. To date, more than one hundred cellulose-binding domains (CBDs) have been classified into at least thirteen families designated I–XIII (Tomme et al. (1995) "Cellulose-Binding Domains: Classification and Properties", in ACS Symposium Series 618 Enzymatic Degradation and Insoluble Carbohydrates, pp. 142–161, Saddler and Penner eds., American Chemical Society, Washington, D.C. (Tomme I); Tomme et al. Adv. Microb. Physiol. (1995) 37:1 (Tomme II); and Smant et al., Proc. Natl. Acad. Sci U.S.A. (1998) 95:4906,–4911, all of which are incorporated herein by reference). Any of the CBDs described in Tomme I or II or any variants thereof, any other presently known CBDs or any new CBDs which may be identified can be used in the present invention. As an illustrative, but in no way limiting example, the CBP or CBD can be from a bacterial, fungal, slime mold, or nematode protein or polypeptide. For a more particular illustrative example, the CBD is obtainable from *Clostridium cellulovorans, Clostridium cellulovorans,* or *Cellulomonas fimi* (e.g., CenA, CenB, CenD, Cex). In addition, the CBD may be selected from a phage display peptide or peptidomimetic library, random or otherwise, using e.g., cellulose as a screening agent. (See Smith Science (1985) 228:1315–1317 and Lam, Nature (1991) 354:82–84). Furthermore, the CBD may be derived by mutation of a portion of a protein or polypeptide which binds to a polysaccharide other than cellulose (or hemicellulose) but also binds cellulose, such as a chitinase, which specifically binds chitin, or a sugar binding protein such as maltose binding protein, rendering said portion capable of binding to cellulose. In any event, the CBD binds cellulose or hemicellulose. Shoseyov and Doi (Proc. Natl. Acad. Sci. USA (1990) 87:2192–2195) isolated a unique cellulose-binding protein (CbpA) from the cellulose "complex" of the cellulolytic bacterium *Clostridium cellulovorans*. This major subunit of the cellulose complex was found to bind to cellulose, but had no hydrolytic activity, and was essential for the degradation of crystalline cellulose. The CbpA gene has been cloned and sequenced (Shoseyov et al. Proc. Natl. Acad. Sci. USA (1992) 89:3483–3487). Using PCR primers flanking the cellulose-binding domain of CbpA, the latter was successfully cloned into an overexpression vector that enabled overproduction of the approximately 17 kDa CBD in *Escherichia coli*. The recombinant CBD exhibits very strong affinity to cellulose and chitin (U.S. Pat. No. 5,496,934; Goldstein et al., J. Bacteriol. (1993) 175:5762; PCT International Publication WO 94/24158, all are incorporated by reference as if fully set forth herein).

In recent years, several CBDs have been isolated from different sources. Most of these have been isolated from proteins that have separate catalytic, i.e., cellulose and cellulose binding domains, and only two have been isolated from proteins that have no apparent hydrolytic activity but possess cellulose-binding activity (Goldstein et al. J. Bacteriol. (1993) 175:5762–5768; Morag et al. Appl. (1995) Environ. Microbiol. 61:1980–1986).

Recombinant proteins:

Any protein for which a gene is known or can be isolated can be used as the recombinant protein and be fused to the cellulose binding peptide according to the present invention. Advantageously, the recombinant protein is of a commercial value. A non-exhaustive list of recombinant proteins which can be manufactured utilizing the process of the present invention and their uses follows.

Thus, for example, glucoamylases and glucose isomerases are used in the food processing industry to convert starch to high fructose corn syrup.

Another useful class of enzymes are proteinases, which are used for the hydrolysis of high molecular weight proteins and which are further used in combination with detergents in cleaning applications, in leather manufacturing processes, in the food industry, and in the manufacture of alcoholic beverages.

Enzymes known as pectinesterases, and several related enzymes, are used for pectin hydrolysis in the food industry.

A class of enzymes known as lipases are used for the cleavage of ester linkages in triglycerides, and are used both in the food industry and for effluent treatment.

The enzyme beta-galactosidase is used industrially for the hydrolysis of whey lactose.

An enzyme known as thermolysin is used in the production of the artificial sweetener aspartame.

An enzyme known as sulphydryl oxidase is used in the reduction of the cooked flavor of milk.

Enzymes known as catalases are used to remove hydrogen peroxides from milk, cheese, and egg processing, and are further used in the sterilization and oxidation of plastics and rubbers.

Heparinases are useful for the production of heparin and heparan sulfate oligosaccharides.

Other proteins, in addition to enzymes, are those which have affinities to other compounds. For example, bacteria, fungi, plants and animals all contain a large number of proteins that exhibit specific interactions with agents such as metal ions and toxic compounds, and have high affinities for such agents.

A class of proteins known as metalloproteins contain prosthetic groups that bind specifically to metal ions. An example of such a prosthetic group is the porphyrin group in hemoglobin. Some other examples of metal ion binding proteins include parvalbumin, which binds to calcium, and metallothionin, an animal protein that binds large amounts of metal ions, especially zinc. Such metal absorptive proteins could also be used for purification in industrial processes.

It is also envisioned that streams of flowing material could be degraded by microbial enzymes. It is known that certain pollutants, whether natural or synthetic, and certain pesticides and other durable organic compounds in the environment can be degraded (inactivated) or converted into useful compounds by microbial enzymes.

It is known, for example, that some microorganisms, for example *Pseudomonas putida*, possessed dehalogenases that are capable of degrading certain pesticides and herbicides, and rendering them less toxic. Similarly, hydrolysis of organophosphate insecticides have been observed by microbial enzymes.

It is also possible to produce antibodies within plant cells. The antibodies can include monoclonal antibodies or fragments thereof having at least a portion of an antigen binding region, including immunoactive entities such as Fv, F(abl)2, Fab fragments (Harlow and Lane, 1988 Antibody, Cold Spring Harbor), single chain antibodies (U.S. Pat. No. 4,946,778), chimeric or humanized antibodies (Morrison et al. Proc. Natl. Acad. Sci. USA (1984) 81:6851; Neuberger et al. Nature (1984) 312:604–608) and complementarily determining regions (CDR).

Another class of proteins are those that bind to antibodies, such as protein-A, protein-G, protein-L and their mutants.

It is also possible to produce protein antibiotics or peptides such as lysozyme or therapeutic proteins which might assist in healing processes, for example, certain wound healing peptides, growth factors and hormones. Proteins such as HSA can also be produced.

Another class of proteins include proteins such as agglutinin, zein, silk, elastine proteins as well as COMP, JUN, FOS and other proteins that may form stable protein-protein interactions such as coiled-coil interactions that may be useful for production of protein fibers.

Another example is the production of animal feed enzymes. Phytase from *Aspergillus niger*, for example, increases the availability of phosphorus from feed for monogastric animals by releasing phosphate from the substrate phytic acid, therefore reducing the need for costly phosphorus supplements. A phytase cDNA was constitutively expressed in transgenic tobacco (*Nicotiana tabacum*) plants (Verwoerd et al., Plant. Physiol. (1995) 109:1199–205). Soybean plants transformed with a fungal phytase gene improve phosphorus availability whereas excretion was decreased for broilers. It appears that phytase can improve growth performance of broilers fed low phosphorous diets when provided either as a commercial supplement or in the form of transformed seeds (Denbow et al., Poult. Sci. (1989) 77:878–881).

Other recombinant proteins of interest, will for the most part be mammalian proteins, and will include blood proteins, such as serum albumin, Factor VII, Factor VIIIc, Factor VIIIvW, Factor IX, Factor X, tissue plasminogen factor, Protein C, von Willebrand factor, antithrombin III, erythropoietin, colony stimulating factors, such as G-, M-, GM-, cytokines, such as interleukins 1–11, integrins, addressing, selecting, homing receptors, surface membrane proteins, such as surface membrane protein receptors, T cell receptor units, immunoglobulins (as further detailed above with respect to antibodies), soluble major histocompatibility complex antigens, structural proteins, such as collagen, fibrin, elastin, tubulin, actin, and myosin, growth factor receptors, growth factors, growth hormone, cell cycle proteins, vaccines, fibrinogen, thrombin, cytokines and hyaluronidase. Additional examples include chymosin, polymerases, saccharidases, dehydrogenases, nucleases, oxido reductases such as fungal peroxidases and lactases, xylanases, rennin, horse radish peroxidase, amylases and soil remediation enzymes.

The genes encoding all of the above listed proteins have been isolated and as such these proteins are readily available for recombinant expression and production according to the teachings of the present invention. It will be appreciated that new genes encoding an ever growing spectrum of proteins are continuously discovered and isolated, rendering such genes available for molecular manipulation and recombinant expression. There is thus no intention to limit the recombinant protein produced utilizing the method of the present invention to any specific protein or list of proteins.

Cellulose binding peptide-recombinant protein fusions:

The fusion of two proteins for which genes has been isolated is well known and practiced in the art. Such fusion involves the joining together of heterologous nucleic acid sequences, in frame, such that translation thereof results in the generation of a fused protein product or a fusion proteins. Methods, such as the polymerase chain reaction (PCR), restriction, nuclease digestion, ligation, synthetic oligonucleotides synthesis and the like are typically employed in various combinations in the process of generating fusion gene constructs. One ordinarily skilled in the art can readily form such constructs for any pair or more of individual proteins. Interestingly, in most cases where such fusion or chimera proteins are produced, and in all cases where one of the proteins was a cellulose binding peptide, both the former and the latter retained their catalytic activity or function.

For example, Greenwood et al. (1989, FEBS Lett. 224:127–131) fused the cellulose binding region of *Cellulomonas fimi* endoglucanase to the enzyme alkaline phosphatase. The recombinant fusion protein retained both its phosphatase activity and the ability to bind to cellulose. For more descriptions of cellulose binding fusion proteins, see U.S. Pat. No. 5,137,819 issued to Kilburn et al., and U.S. Pat. No. 5,719,044 issued to Shoseyov et al. both incorporated by reference herein. See also U.S. Pat. No. 5,474,925. All of which are incorporated herein by reference.

The recombinant protein immobilized via its fused counterpart to the cellulosic matter can be released from the plant derived cellulosic matter by cleavage thereof, e.g., by proteolysis, using either a nonspecific general protease such as proteinase K or trypsin, or a specific protease as further detailed hereinunder. For example, release can be effected by treatment with proteinase K at a concentration of about 50 μg/ml for about 20 minutes at about 37° C. (Din et al. Bio/Technology (1991) 9:1096–1099).

Inclusion of a dedicated cleavage site:

According to a preferred embodiment of the present invention the fusion protein includes the recombinant protein and the cellulose binding peptide separated therebetween via a unique amino acid sequence recognizable and digestible by a protease or under predetermined cis or trans conditions for digesting a controllable intervening protein sequence.

As used herein in the specification and in the claims section that follows, the phrase "unique amino acid sequence recognizable and digestible by a protease" includes a protease recognition sequence which is both recognizable and readily accessible to a protease. Thus, the unique sequence can be a solitary sequence (i.e., which does not appear in the recombinant protein and optionally also not in the cellulose binding peptide) or alternatively, the sole sequence of several similar sequences which is not sequestered from the protease due to the tertiary structure of the recombinant protein and optionally the cellulose binding peptide. In both these cases proteolysis will release the recombinant protein from the fusion protein cellulosic matter complex.

As used herein in the specification and in the claims section that follows, the phrase "controllable intervening protein sequence" includes unique amino acid sequences capable of excision from or cleavage of a peptide under predetermined conditions in cis or in trans, e.g., increase in temperature, exposure to light, unblocking of amino acid residues by dephosphorylation and treatment with chemical reagents or deglycosylation, examples include proteolysis effected under acidic conditions (HCl, e.g., to cleave between Asp and Pro) and proteolysis effected by a proteolysing reagent, such as CNBr to cleave downstream of Met, all as known in the art and/or as further described in U.S. Pat. No. 5,834,247, which is incorporated herein by reference.

Thus, according to an aspect of the present invention there is provided a composition of matter comprising (a) a plant derived cellulosic matter; and (b) a fusion protein including a recombinant protein and a cellulose binding peptide separated therebetween via a unique amino acid sequence recognizable and digestible by a protease or under predetermined cis or trans conditions for digesting a controllable intervening protein sequence, wherein the fusion protein is complexed to the plant derived cellulosic matter by affinity binding via the cellulose binding peptide.

Nucleic acid molecules which can be used according to preferred embodiments of the present invention to express the fusion protein in plant cells would therefore include a heterologous nucleic acid sequence including (i) a first sequence encoding a cellulose binding peptide; (ii) a second sequence encoding a recombinant protein, wherein the first and second sequences are joined together in frame in either orientation; and (iii) a third sequence encoding a unique amino acid sequence recognizable and digestible by a protease or under predetermined cis or trans conditions for digesting a controllable intervening protein sequence, the third sequence is between and in frame with the first and second sequences.

Thus, specific cleavage can be used to release the recombinant protein from the fusion protein cellulosic matter complex. For example, one can include a protease recognition site or a chemical cleavage site between the recombinant protein and the cellulose binding peptide. Examples of recognition sites include those for collagenase, thrombin, enterokinase, and Factor $X_a$ which are cleaved specifically by the respective enzymes. Chemical cleavage sites sensitive, for example, to low pH or cyanogen bromide, can also be used.

Where cleavage is used, the recombinant protein can be cleaved readily from the cellulosic matter by the use of a protease specific for a sequence present therebetween and the cellulose binding peptide.

It will be appreciated in this respect that four main classes of specific proteases are known, including (i) cysteine proteases, including cathepsin B and L; (ii) aspartyl protease cathepsin D; (iii) serine proteases including plasmin, tissue-type plasminogen activator (tPA) and urokinase-type plasminogen activator (uPA), and (iv) matrix metalloproteinases (MMPs), including collagenases, gelatinases A and B (MMP2 and MMP9) and stromelysin (MMP3). Members of these protease families are commercially available and their recognition sequences known. As such, these proteases can be used to implement the step of releasing the recombinant protein from the plant derived cellulosic matter while implementing the process according to the present invention.

Genetically modified plant material:

According to an aspect of the present invention there is provided a nucleic acid molecule comprising (a) a promoter sequence for directing protein expression in plant cells; and (b) a heterologous nucleic acid sequence as further detailed herein, wherein, the heterologous nucleic acid sequence is down stream the promoter sequence, such that expression of the heterologous nucleic acid sequence is effectable by the promoter sequence. Such a nucleic acid molecule needs to be effectively introduced into plant cells, so as to genetically modify the plant.

There are various methods of introducing foreign genes into both monocotyledonous and dicotyledenous plants (Potrykus, I., Annu. Rev. Plant. Physiol., Plant. Mol. Biol. (1991) 42:205–225; Shimamoto et al., Nature (1989) 338:274–276). The principle methods of causing stable integration of exogenous DNA into plant genomic DNA include two main approaches:

(i) Agrobacterium-mediated gene transfer: Klee et al. (1987) Annu. Rev. Plant Physiol. 38:467–486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2–25; Gatenby, in Plant Biotechnology, eds. Kung, S. and Arntzen, C. J., Butterworth Publishers, Boston, Mass. (1989) p. 93–112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52–68; including methods for direct uptake of DNA into protoplasts, Toriyama, K. et al. (1988) Bio/Technology 6:1072–1074. DNA uptake induced by brief electric shock of plant cells: Zhang et al. Plant Cell Rep. (1988) 7:379–384. Fromm et al. Nature (1986) 319:791–793. DNA injection into plant cells or tissues by particle bombardment, Klein et al. Bio/Technology (1988) 6:559–563; McCabe et al. Bio/Technology (1988) 6:923–926; Sanford, Physiol. Plant. (1990) 79:206–209; by the use of micropipette systems: Neuhaus et al., Theor. Appl. Genet. (1987) 75:30–36; Neuhaus and Spangenberg, Physiol. Plant. (1990) 79:213–217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197–209; and Ohta, Proc. Natl. Acad. Sci. USA (1986) 83:715–719.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1–9. The Agrobacterium system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transgenic plant be produced such that the regenerated plant has the identical traits and characteristics of the parent transgenic plant, e.g., a reproduction of the fusion protein. Therefore, it is preferred that the transgenic plant be regenerated by micropropagation which provides a rapid, consistent reproduction of the transgenic plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transgenic plantlets are transferred to a greenhouse for hardening where the plants' tolerance to light is gradually increased so that it can be grown in the natural environment.

The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous sequence is not readily amenable to detection, the construct will preferably also have a selectable marker gene suitable for determining if a plant cell has been transformed. A general review of suitable markers for the members of the grass family is found in Wilmink and Dons, Plant Mol. Biol. Reptr. (1993) 11:165–185.

Sequences suitable for permitting integration of the heterologous sequence into the plant genome are also recommended. These might include transposon sequences and the like for homologous recombination as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include an expression cassette for expression of the fusion protein of interest. Usually, there will be only one expression cassette, although two or more are feasible. The recombinant expression cassette will contain in addition to the heterologous sequence one or more of the following sequence elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

Viral infected plant material:

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Viruses that have been shown to be useful for the transformation of plant hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172–189 (1988). Pseudovirus particles for use in expressing foreign DNA in many hosts, including plants, is described in WO 87/06261.

Construction of plant RNA viruses for the introduction and expression of non-viral foreign genes in plants is demonstrated by the above references as well as by Dawson, W. O. et al., Virology (1989) 172:285–292; Takamatsu et al.

EMBO J. (1987) 6:307–311; French et al. Science (1986) 231:1294–1297; and Takamatsu et al. FEBS Letters (1990) 269:73–76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a fusion protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomie promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired fusion protein.

Fusion protein compartmentalization—signal peptides:

As already mentioned hereinabove, compartmentalization of the fusion protein is an important feature of the present invention because it allows undisturbed plant growth. Thus, according to one aspect of the present invention, the fusion protein is compartmentalized within cells of the plant or cultured plant cells, so as to be sequestered from cell walls of the cells of the plant or cultured plant cells.

The fusion protein can be compartmentalized within a cellular compartment, such as, for example, the cytoplasm, endoplasmic reticulum, golgi apparatus, oil bodies, starch bodies, chloroplastids, chloroplasts, chromoplastids, chromoplasts, vacuole, lysosomes, mitochondria or the nucleus.

Accordingly, the heterologous sequence used while implementing the process according to this aspect of the present invention includes (i) a first sequence encoding a cellulose binding peptide; (ii) a second sequence encoding a recombinant protein, wherein the first and second sequences are joined together in frame; and (iii) a third sequence encoding a signal peptide for directing a protein to a cellular compartment, the third sequence being upstream and in frame with the first and second sequences.

The following provides description of signal peptides which can be used to direct the fusion protein according to the present invention to specific cell compartments.

It is well-known that signal peptides serve the function of translocation of produced protein across the endoplasmic reticulum membrane. Similarly, transmembrane segments halt translocation and provide anchoring of the protein to the plasma membrane, see, Johnson et al. The Plant Cell (1990) 2:525–532; Sauer et al. EMBO J. (1990) 9:3045–3050; Mueckler et al. Science (1985) 229:941–945. Mitochondrial, nuclear, chloroplast, or vacuolar signals target expressed protein correctly into the corresponding organelle through the secretory pathway, see, Von Heijne, Eur. J. Biochem. (1983) 133:17–21; Yon Heijne, J. Mol. Biol. (1986) 189:239–242; Iturriaga et al. The Plant Cell (1989) 1:381–390; McKnight et al., Nucl. Acid Res. (1990) 18:4939–4943; Matsuoka and Nakamura, Proc. Natl. Acad. Sci. USA (1991) 88:834–838. A recent book by Cunningham and Porter (Recombinant proteins from plants, Eds. C. Cunningham and A. J. R. Porter, 1998 Humana Press Totowa, N.J.) describe methods for the production of recombinant proteins in plants and methods for targeting the proteins to different compartments in the plant cell. In particular, two chapters therein (14 and 15) describe different methods to introduce targeting sequences that results in accumulation of recombinant proteins in compartments such as ER, vacuole, plastid, nucleus and cytoplasm. The book by Cunningham and Porter is incorporated herein by reference. Presently, the preferred site of accumulation of the fusion protein according to the present invention is the ER using signal peptide such as Cel 1 or the rice amylase signal peptide at the N-terminus and an ER retaining peptide (HDEL, SEQ ID NO:1; or KDEL, SEQ ID NO:2) at the C-terminus.

Promoters and control of expression:

Any promoter which can direct the expression of the fusion protein according to the present invention can be utilized to implement the process of the instant invention, both constitutive and tissue specific promoters. According to presently preferred embodiment the promoter selected is constitutive, because such a promoter can direct the expression of higher levels of the fusion protein. In this respect the present invention offers a major advantage over the teachings of U.S. Pat. No. 5,474,925 in which only tissue specific and weak promoters can be employed because of the deleterious effect of the fusion protein described therein on cell wall development. The reason for which the present invention can utilize strong and constitutive promoters relies in the compartmentalization and sequestering approach which prohibits contact between the expressed fusion protein and the plant cell walls which such walls are developing.

Constitutive and tissue specific promoters, CaMV35S promoter (Odell et al. Nature (1985) 313:810–812) and ubiquitin promoter (Christensen and Quail, Transgenic research (1996) 5:213–218) are the most commonly used constitutive promoters in plant transformations and are the preferred promoters of choice while implementing the present invention.

In corn, within the kernel, proteins under the ubiquitin promoters, are preferentially accumulated in the germ (Kusnadi et al., Biotechnol. Bioeng. (1998) 60:44–52). The amylose-extender (Ae) gene encoding starch-branching enzyme IIb (SBEIIb) in maize is predominantly expressed in endosperm and embryos during kernel development (Kim et al. Plant. Mol. Biol. (1998) 38:945–956). A starch branching enzyme (SBE) showed promoter activity after it was introduced into maize endosperm suspension cells by particle bombardment (Kim et al. Gene (1998) 216:233–243). In transgenic wheat it has been shown that a native HMW-GS gene promoter can be used to obtain high levels of expression of seed storage and, potentially, other proteins in the endosperm (Blechl and Anderson, Nat. Biotechnol. (1996) 14:875–9). Polygalacturonase (PG) promoter was shown to confer high levels of ripening-specific gene expression in tomato (Nicholass et al. Plant. Mol. Biol. (1995) 28:423–435). The ACC oxidase promoter (Blume and Grierson, Plant. J. (1997) 12:731–746) represents a promoter from the ethylene pathway and shows increased expression during fruit ripening and senescence in tomato. The promoter for tomato 3-hydroxy-3-methylglutaryl coenzyme A reductase gene accumulates to high level during fruit ripening (Daraselia et al. Plant. Physiol. (1996) 112:727–733). Specific protein expression in potato tubers can be mediated by the patatin promoter (Sweetlove et al. Biochem. J. (1996) 320:487–492). Protein linked to a chloroplast transit peptide changed the protein content in transgenic soybean and canola seeds when expressed from a seed-specific promoter (Falco et al. Biotechnology (NY) (1995) 13:577–82). The seed specific bean phaseolin and soybean beta-conglycinin promoters are also suitable for the latter example (Keeler et al. Plant. Mol. Biol. (1997) 34:15–29). Promoters that are expressed in plastids are also suitable in conjunction with plastid transformation.

Each of these promoters can be used to implement the process according to the present invention.

Thus, the plant promoter employed can a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, Arabidopsis ACT2/ACT8 actin promoter, Arabidopsis ubiquitin UBQ1 promoter, barley leaf thionin BTH6 promoter, and rice actin promoter.

Examples of tissue specific promoters include, without being limited to, bean phaseolin storage protein promoter, DLEC promoter, PHSβ promoter, zein storage protein promoter, conglutin gamma promoter from soybean, AT2S1 gene promoter, ACT11 actin promoter from Arabidopsis, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr303J and str246C active in pathogenic stress.

Expression follow up:

Expression of the fusion protein can be monitored by a variety of methods. For example, ELISA or western blot analysis using antibodies specifically recognizing the recombinant protein or its cellulose binding peptide counterpart can be employed to qualitatively and/or quantitatively monitor the expression of the fusion protein in the plant. Alternatively, the fusion protein can be monitored by SDS-PAGE analysis using different staining techniques, such as, but not limited to, coomasie blue or silver staining. Other methods can be used to monitor the expression level of the RNA encoding for the fusion protein. Such methods include RNA hybridization methods, e.g., Northern blots and RNA dot blots.

Binding of the fusion protein to the plant derived cellulosic matter:

When sufficient expression has been detected, binding of the fusion protein to the plant derived cellulosic matter is effected. Such binding can be achieved, for example, as follows. Whole plants, plant derived tissue or cultured plant cells are homogenized by mechanical method in the presence or absence of a buffer, such as, but not limited to, PBS. The fusion protein is therefore given the opportunity to bind to the plant derived cellulosic matter. Buffers that may include salts and/or detergents at optimal concentrations may be used to wash non specific proteins from the cellulosic matter.

Extraction and purification:

In general, a recent book by Cunningham and Porter (Recombinant proteins from plants, Eds. C. Cunningham and A. J. R. Porter, 1998 Humana Press Totowa, N.J.) describes methods for the production of recombinant proteins in plants including methods for extraction of the proteins from the plants. The methods used herein for extraction of proteins from plants are similar, however the ability of the fusion protein to bind to cellulose dictates its fate, unless extraction is done under condition in which the cellulose binding peptide do not bind to cellulose, for example, pH higher than 10 (for most CBDs) or high concentration of glucose or cellobiose (200 mM or higher) for family IX CBDs. If the initial extraction is conducted under conditions that prevent binding, the supernatant is cleared from the cellulosic matter and then the solution is brought by either dilution, dialysis or pH correction, if necessary, to a condition that enables binding, after which cellulose is added in a batch or the solution is loaded on a cellulose column. Cellulose affinity purification is conducted as described, for example, in U.S. Pat. Nos. 5,719,044; 5,670,623; 5,856,021; 5,137,819; 5,202,247; 5,340,731; and 5,474,925; and U.S. patent application Ser. No. 08/788,621; and 08/788,622; EP 0 381 719 B1, and EP application No. 93907724.4. Alternatively, the extraction solution provides conditions that favor binding to the plant derived cellulosic matter.

In any case, while the fusion protein is bound to cellulose, further whases can be employed for further removal of unbound proteins, conditions which dissociate such binding or proteolytic cleavage can be used to isolate the fusion protein itself, or proteolytic cleavage can be used to isolate the recombinant protein, all as further detailed hereinabove.

Additional objects, advantages, and novel features of the present invention will become apparent to one ordinarily skilled in the art upon examination of the following examples, which is not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., molecular Cloning—A Laboratory Manual, Cold Spring Harbor Laboratory, Cold Spring Harbor, N.Y. (1989). Other general references are provided throughout this document. The procedures therein are believed to be well known in the art and are provided for the convenience of the reader. All the information contained therein, as well as that contained in the Manual by Sambrok et al., is incorporated herein by reference.

Example 1

Expression of CBD-Protein-L in Transgenic Potato Tubers Constructs

A vector containing the class-I patatin gene B33 promoter (Olesinski et al., 1996, Plant Phisiol. 111:541–550), fused to the cell signal sequence (Shani et al., 1997, Plant Mol. Biol. 34:837–842), protein-L (hereinafter ProtL, Nilson et al., 1993, J. Immunol. Meth. 164:33–40), CBD cex sequence (Gilkes et al., 1991, Microbiol. Rev. 55:303–315) and HDEL (SEQ ID NO:1) retaining peptide sequence was constructed as follows.

A DNA fragment encoding the cell signal peptide (nucleotide 1–105 of SEQ ID NO:3) was generated by PCR using the following primers: No. 1 (BglII) 5'-AAAAAGATCTATGGCGCGAAAATCACTAA-3' (SEQ ID NO:4) and No. 2 (XbaI) 5'-AAAATCTAGATTTACGGAGAGCGTCGCG-3' (SEQ ID NO:5). A DNA fragment encoding the ProtL-CBDcex (nucleotides 3–1280 of SEQ ID NO:6) was generated by PCR using the following primers: No. 3 (XbaI) 5'-AAAATCTAGAATGGCGGCGGTAGAAAATAAAG-3' (SEQ ID NO:7); and No. 4 (HDEL, Stop and SalI) 5'-AAAAGTCGACTTAAAGTTCATCATGCTCGACG CCGACCGTGCA-3' (SEQ ID NO:8). The two fragment were digested with BglII, XbaI and SalI and ligated in one step into pUC19 (New England Biolabs, Beverly, Mass.) that was pre digested with BamHI and SalI. The primer for the c-terminal end of the ProtL-CBD contained the retaining peptide sequence HDEL (SEQ ID NO:1) and a stop codon in frame. The DNA containing the Ccll Signal-ProtL-CBD-HDEL (hereinafter, ProtL-CBD) fusion was excised using SmaI and SalI and was subcloned into the SmaI and SalI sites of the binary vector Bin19 (Bevan, 1984, Nuc. Acid Res. 12:8711–8721) under the class-I patatin gene B33 promoter (Olesinski et al., 1996, Plant Phisiol. 111:541–550).

Construction of transgenic plants:

The binary vector was mobilized into disarmed LB 4404 *Agrobacterium tumefaciens* (An, 1987, Meth. Enzymol. 153:292–305). Tuber discs transformation was performed with Solanum tuberosum cv Desiree plants as described previously (Olesinski et al., 1996, 1996, Plant Phisiol. 111:541–550). Regenerated transgenic plants were selected on kanamycin.

Analysis of transgenic plants:

Transformant plants were selected by rooting on kanamycin (100 mg/L). Growth conditions in growth room and green house were as described previously (Olesinski et al., 1996, 1996, Plant Phisiol. 111:541–550).

Transgenic plants transformed with the ProtL-CBD construct can be tested for expression of ProtL-CBD. Thus, for example, a Northern blot analysis of ProtL-CBD RNA expression can be carried out using the DNA fragment of SEQ ID NO:3 or a portion thereof as a probe. Furthermore, RT-PCR can be performed on RNA samples obtained from such transgenic plants using PCR primers No. 3 and No. 4 to amplify and detect the ProtL-CBD RNA. Additional methods for analysis of expression in transgenic plants include RNase protection assays. Expression of the ProtL-CBD fusion protein can alternatively or additionally be evaluated by monitoring the fusion protein itself using, for example, ELISA or Western blot protocols and anti-CBD or ProtL antibodies. Yet in addition, the ProtL-CBD fusion protein can be visualized by SDS-PAGE analysis using different staining techniques, such as coomasie blue or silver staining, immuno precipitation, enzyme linked immunoassays or CBD and ProtL binding assays. In addition, techniques such as in situ hybridization and immunostaining also may be used to detect the presence or expression of the recombinant construct in specific plant organs and tissues. The methods for performing all of these assays are well known to those skilled in the art.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. A process of producing a protein of interest in a plant, plant derived tissue or cultured plant cells and of isolating the protein from the plant, plant derived tissue or cultured plant cells, the process comprising the steps of:
   (a) providing a plant, a plant derived tissue or cultured plant cells expressing a fusion protein including the protein of interest and a cellulose binding peptide being fused thereto, said fusion protein being compartmentalized within cells of said plant, plant derived tissue or cultured plant cells, so as to be sequestered from cell walls of said cells of said plant, plant derived tissue or cultured plant cells;
   (b) homogenizing said plant, plant derived tissue or cultured plant cells, so as to bring into contact said fusion protein with a plant derived cellulosic matter of said plant, plant derived tissue or cultured plant cells, to thereby effect affinity binding of said fusion protein via said cellulose binding peptide to said cellulosic matter, thereby obtaining a fusion protein cellulosie matter complex; and (c) isolating said fusion protein cellulosic matter complex.

2. The process of claim 1, further comprising the step of:

(d) washing said fusion protein cellulosic matter complex, thereby removing endogenous plant proteins and other plant material therefrom.

3. The process of claim 2, further comprising the step of:

(e) collecting said fusion protein cellulosic matter complex as a final product of the process.

4. The process of claim 2, further comprising the step of:

(e) exposing said fusion protein cellulosic matter complex to conditions effective in dissociating said fusion protein from said cellulosic matter; and (f) isolating said fusion protein, thereby obtaining an isolated fusion protein.

5. The process of claim 4, wherein said conditions effective in dissociating said fusion protein from said cellulosic matter are selected from the group consisting of basic conditions, denaturative conditions and affinity displacement conditions.

6. The process of claim 4, further comprising the step of:

(g) exposing said isolated fusion protein to conditions effective in digesting said fusion protein so as to release said protein of interest from said fusion protein, thereby obtaining a released protein of interest.

7. The process of claim 6, wherein said conditions effective in digesting said fusion protein so as to release said protein of interest therefrom are selected from the group consisting of proteolysis effected via a protease and proteolysis effected under predetermined cis or trans conditions for digesting a controllable intervening protein sequence.

8. The process of claim 6, further comprising the step of:

(h) isolating said released protein of interest.

9. The process of claim 2, further comprising the step of:

(e) exposing said fusion protein cellulosic matter complex to conditions effective in digesting said fusion protein so as to release said protein of interest therefrom, thereby obtaining a released protein of interest.

10. The process of claim 9, wherein said conditions effective in digesting said fusion protein so as to release said protein of interest therefrom are selected from the group consisting of proteolysis effected via a protease and proteolysis effected under predetermined cis or trans conditions for digesting a controllable intervening protein sequence.

11. The process of claim 9, further comprising the step of:

(f) isolating said released protein of interest.

* * * * *

SEQUENCE LISTING

<160> NUMBER OF SEQ ID NOS: 8

<210> SEQ ID NO 1
<211> LENGTH: 4
<212> TYPE: PRT
<213> ORGANISM: Artificial sequence
<220> FEATURE:
<223> OTHER INFORMATION: ER retaining signal peptide

<400> SEQUENCE: 1

His Asp Glu Leu
1

<210> SEQ ID NO 2
<211> LENGTH: 4
<212> TYPE: PRT
<213> ORGANISM: Artificial sequence
<220> FEATURE:
<223> OTHER INFORMATION: ER retaining signal peptide

<400> SEQUENCE: 2

Lys Asp Glu Leu
1

<210> SEQ ID NO 3
<211> LENGTH: 150
<212> TYPE: DNA
<213> ORGANISM: Arabidopsis thaliana

<400> SEQUENCE: 3

```
atggcgcgaa aatccctaat tttcccggtg attttgctcg ccgttcttct cttctctccg      60
ccgatttact ccgccggtca cgattaccgc gacgctctcc gtaaaagcat tctcttcttc     120
gaaggtcaac gttccggtaa actccctcca                                      150
```

<210> SEQ ID NO 4
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 4

```
aaaaagatct atggcgcgaa aatcactaa                                        29
```

<210> SEQ ID NO 5
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 5

```
aaaatctaga tttacggaga gcgtcgcg                                         28
```

<210> SEQ ID NO 6
<211> LENGTH: 1305
<212> TYPE: DNA
<213> ORGANISM: Artificial sequence
<220> FEATURE:
<223> OTHER INFORMATION: Construct containing Protein L, fused to
      CBDcex sequence

<400> SEQUENCE: 6

```
                                                    -continued ccatggcggc ggtagaaaat aaagaagaaa caccagaaac accagaaact gattcagaag      60
aagaagtaac aatcaaagct aacctaatct ttgcaaatgg aagcacacaa actgcagaat     120
tcaaaggaac atttgaaaaa gcaacatcag aagcttatga gtatgcagat actttgaaga    180
aagacaatgg agaatatact gtagatgttg cagataaagg ttatacttta aatattaaat    240
ttgctggaaa agaaaaaaca ccagaagaac caaagaagaa agttactatt aaagcaaact    300
taatctatgc agatggaaaa acacaaacag cagaattcaa aggaacattt gaagaagcaa    360
cagcagaagc atacagatat gcagatgcat taaagaagga caatggagaa tatacagtag    420
acgttgcaga taaaggttat actttaaata ttaaatttgc tggaaaagaa aaaacaccag    480
aagaaccaaa agaagaagtt actattaaag caaacttaat ctatgcagat ggaaaaacac    540
aaacagcaga attcaaagga acatttgaag aagcaacagc agaagcatac agatatgctg    600
acttattagc agcaaaagaa aatggtaaat atacagtaga cgttgcagat aaaggttata    660
ctttaaatat taaatttgct ggaaaagaaa aaacaccaga agaaccaaaa gaagaagtta    720
ctattaaagc aaacttaatc tatgcagatg gaaaaactca aacagcagag ttcaaaggaa    780
catttgcaga agcaacagca gaagcataca gatacgctga cttattagca aaagaaaatg    840
gtaaatatac agcagactta gaagatggtg gatacactat taatattaga tttgcaggta    900
agaaagttga cgaaaaacca gaagggatcc ctccgacgcc gaccccgact agtggtccgg    960
ccgggtgcca ggtgctgtgg ggcgtcaacc agtggaacac cggcttcacc gcgaacgtca   1020
ccgtgaagaa cacgtcctcc gctccggtag acggctggac gctcacgttc agcttcccgt   1080
ccggccagca ggtcacccag gcgtggagct cgacggtcac gcagtccggc tcggccgtga   1140
cggtccgcaa cgccccgtgg aacggctcga tcccggcggg cggcaccgcg cagttcggct   1200
tcaacggctc gcacacgggc accaacgccg cgccgacggc gttctcgctc aacggcacgc   1260
cctgcacggt cggcgtcgag caccaccacc accaccacca ccact                   1305

<210> SEQ ID NO 7
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 7
aaaatctaga atggcggcgg tagaaaataa ag                                    32

<210> SEQ ID NO 8
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 8
aaaagtcgac ttaaagttca tcatgctcga cgccgaccgt gca                        43
```